US009993565B2

United States Patent
Grouard-Vogel et al.

(10) Patent No.: US 9,993,565 B2
(45) Date of Patent: Jun. 12, 2018

(54) METHOD FOR TREATING IFNALPHA RELATED CONDITIONS

(75) Inventors: Geraldine Grouard-Vogel, Paris (FR); Olivier Dhellin, Paris (FR); Bernard Fanget, Chateauneuf (FR); Pierre Vandepapeliere, Bonnine (BE); Camille Roucairol, Paris (FR)

(73) Assignee: NEOVACS, Paris (FR)

( * ) Notice: Subject to any disclaimer, the term of this patent is extended or adjusted under 35 U.S.C. 154(b) by 0 days. days.

(21) Appl. No.: 14/110,312

(22) PCT Filed: Apr. 4, 2012

(86) PCT No.: PCT/EP2012/056238
§ 371 (c)(1),
(2), (4) Date: Oct. 7, 2013

(87) PCT Pub. No.: WO2012/136739
PCT Pub. Date: Oct. 11, 2012

(65) Prior Publication Data
US 2014/0023617 A1    Jan. 23, 2014

Related U.S. Application Data

(60) Provisional application No. 61/472,854, filed on Apr. 7, 2011.

(30) Foreign Application Priority Data

Apr. 7, 2011  (EP) .................................. 11305408
Nov. 7, 2011  (EP) .................................. 11188125

(51) Int. Cl.
A61K 47/48       (2006.01)
A61K 38/21       (2006.01)
(Continued)

(52) U.S. Cl.
CPC ...... *A61K 47/48284* (2013.01); *A61K 38/212* (2013.01); *A61K 39/0008* (2013.01);
(Continued)

(58) Field of Classification Search
None
See application file for complete search history.

(56) References Cited

U.S. PATENT DOCUMENTS 4,877,612 A      10/1989  Berger et al.
2004/0028647 A1   2/2004  Zagury et al.
(Continued)

FOREIGN PATENT DOCUMENTS

EP    109 942 B1    3/1991
EP    180 564 B1    7/1991
(Continued)

OTHER PUBLICATIONS

NCT01058343 (2010), p. 1-4.*
(Continued)

*Primary Examiner* — Vanessa L. Ford
*Assistant Examiner* — Jegatheesan Seharaseyon
(74) *Attorney, Agent, or Firm* — Young & Thompson

(57) ABSTRACT

An immunogenic product including IFNα coupled to a carrier protein molecule is capable to induce in vivo anti-IFNα antibodies and is useful in treating IFNα related conditions.

13 Claims, 5 Drawing Sheets

Days after first immunization

(51) Int. Cl.
A61K 39/00 (2006.01)
A61K 47/64 (2017.01)
(52) U.S. Cl.
CPC .......... *A61K 47/643* (2017.08); *A61K 47/646* (2017.08); *A61K 2039/6081* (2013.01); *C12N 2760/20031* (2013.01)

(56) References Cited

U.S. PATENT DOCUMENTS

| | | |
|---|---|---|
| 2006/0013800 A1 | 1/2006 | Le Buanec et al. |
| 2006/0067944 A1 | 3/2006 | Le Buannec et al. |
| 2007/0202102 A1 | 8/2007 | Bizzini et al. |

FOREIGN PATENT DOCUMENTS

| | | |
|---|---|---|
| EP | 231 039 B1 | 1/1992 |
| GB | 2 189 141 A | 10/1987 |
| WO | 1995005845 | 3/1995 |

OTHER PUBLICATIONS

Zagury et al. (2009), PNAS, vol. 109, No. 13, pp. 5294-5299.*
Gringeri et al. (1994), J. Acq. Immune Deficiency Synd., vol. 7, No. 9, pp. 978-988.*
Emamaullee et al. (2009), vol. 58, pp. 1302-1311.*
Hosmalin et al. (2006), vol. 80, pp. 984-993.*
Van Boxel-Dezaire et al., "Complex Modulation of Cell Type-Specific Signaling in Response to Type I Interferons", Immunity, 2006, vol. 25, pp. 361-372.
Baccala et al., "Interferoris as pathogenic effectors in autoimmunity", Immunological Reviews, 2005, vol. 204, pp. 9-26.
Dall'Era et al., "Type I interferon correlates with serological and clinical manifestations of SLE", Ann Rheum Dis, 2005, vol. 64, pp. 1692-1697.
Sedaghat et al. "Chronic CD4 T-Cell Activation and Depletion in Human Immunodeficiency Virus Type 1 Infection: Type I Interferon-Mediated Disruption of T-Cell Dynamics", Journal of Virology, 2008, vol. 82, No. 4, pp. 1870-1883.
Mandl et al , "Divergent TLR7 and TLR9 signaling and type I interferon production distinguish pathogenic and nonpathogenic AIDS virus infections", Nature Medicine, 2008, vol. 14, pp. 1077-1087.
De Groot et al., "Immunogenicity of protein therapeutics", Trends in Immunology, 2007, vol. 28, No. 11, pp. 482-490.
Pestka et al., "Interferons; interferon-like cytokines, and their receptors", Immunological Reviews, 2004 vol. 202, pp. 8-32.
Mire-Sluis et al., "Recommendations for the design and optimization of immunoassays used in the detection of host antibodies against biotechnology products", 2004, Journal Immunological Methods, vol. 289, pp. 1-16.
McGhee et al., "New Perspectives in Mucosal Immunity with Emphasis on Vaccine Development", Seminars in Hematology, 1993, vol. 30, No. 4, Suppl. 4. pp. 3-15.
Bovarnik et al., "The Influence of Certain Salts, Amino Acids, Sugars, and Proteins on the Stability of Rickettsiae", J. Bacteriology, 1950, vol. 59, pp. 509.
Yao et al., "Neutralization of Interferon-alpha/beta-Inducible Genes and Downstream Effect in a Phase I Trial of an Anti-Interferon-alpha Monoclonal Antibody in Systemic Lupus Erythematosus", Arthritis Rheumatism, 2009, vol. 60, No. 6, pp. 1785-1796.
Mathian et al., "Active immunisation of human interferon α transgenic mice with a human interferon α Kinoid induces antibodies that neutralise interferon α in sera from patients with systemic lupus erythematosus", Ann Rheum Dis., 2011, vol. 70, pp. 1138-1143.
Crow, Mary K., "Interferon-alpha: a therapeutic target in systemic lupus erythematosus", Rheum Dis Clin North Am., 2010, vol. 36, No. 1, pp. 173-186.
Crow, Mary K., "Type I interferon in organ-targeted autoimmune and inflammatory diseases", Crow Arthritis Research & Therapy, 2010, vol. 12, Suppl. 1, pp. 55-65.
Bizzini et al, "Kinoids: a family of immunogens for active anticytokine immunotherapy applied to autoimmune diseases and cancer" Immunotherapy. 2010, 2(3):347-385, Paris, France.
Hardy et al., "Interferon-alpha Is the Primary Plasma Type-I IFN in HIV-1 Infection and Correlates with Immune Activation and Disease Markers", PLOS ONE, www.plosone.org, Feb. 1, 2013, vol. 8, Issue 2, pp. 1-9, Cape Town, South Africa.
Sedaghat et al., "Chronic CD4+T-Cell Activation and Depletion in Human Immunodeficiency Virus Type 1 Infection: Type I Interferon-Mediated Disruption of T-Cell Dynamics", Journal of Virology, Feb. 2008, vol. 82, No. 4, p. 1870-1883, Baltimore, Maryland.
Papatriantafyllou, "The Interferon Paradox", Nature Reviews Immunology, vol. 13, Jun. 2013, AOP, published online May 7, 2013; Macmillan Publishers Limited.
Ferreira et al., "A Type I Interferon Transcriptional Signature Precedes Autoimmunity in Children Genetically at Risk for Type 1 Diabetes", Diabetes, vol. 63, Jul. 2014, pp. 2538-2550, Cambridge, U.K.
Foulis et al., "Immunoreactive alpha-Interferon in Insulin-Secreting beta Cells in Type 1 Diabetes Mellitus", The Lancet, Dec. 19, 1987, pp. 1423-1427, Hertfordshire, U.K.
Huang et al., "Interferon Expression in the Pancreases of Patients With Type I Diabetes", Diabetes, vol. 44, Jun. 1995, pp. 658-664, San Francisco, California.
Stewart et al., "Induction of Type I Diabetes by Interferon-alpha in Transgenic Mice", Science, vol. 260, Jun. 25, 1993, pp. 1942-1946; New York, New York.
Li et al., "The role of interferon alpha in initiation of type I diabetes in the NOD mouse", Clinical Immunology, 2011, vol. 140, pp. 3-7, Stanford, California.
FDA, "Guidance for Industry, Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Jul. 2005, Pharmacology and Toxicology, Rockville, Maryland.
Bizzini et al, "Kinoids: A Family of Immunogens for Active Anticytokine Immunotherapy Applied to Autoimmune Diseases and Cancer" Immunotherapy. 2010, 2(3):347-365.

* cited by examiner

METHOD FOR TREATING IFNALPHA RELATED CONDITIONS

FIELD OF INVENTION

The present invention relates to an immunogenic vaccine and its use for treating IFNα related conditions such as systemic lupus erythematosus.

BACKGROUND OF INVENTION

The IFN type I family includes IFNα, IFNβ, IFNδ, IFN1, IFNκ, IFNτ, and IFNω̄. The predominant forms are IFNα, of which 13 closely related proteins are described in humans, and the single IFNβ. Despite the fact that different IFN type I forms may promote different biological responses, all IFN type I are structurally related (their genes lack introns and are located on the short arm of chromosome 9) and signal through the same receptor subunits (Van Boxel-Dezaire et al., Immunity 2006; 25:361-372).

The interest on the relationship between IFN type I and autoimmune disorders is nowadays increasing, since the signs of its induction, the so-called interferon signature, have been recently reported in patients suffering from different autoimmune diseases (Baccala et al. Immunol Rev 2005; 204:9-26). In fact, due to its immune-modulator effects, IFN type I seems to be involved in several pathogenic pathways of various autoimmune conditions.

The paradigm of IFN type I pathogenic relevance in autoimmunity is systemic lupus erythematosus (SLE). SLE is a chronic disease, characterized by a multi-organ involvement, due to a paradoxical damage of organs caused by autoantibodies directed to self-antigens. The etiology of SLE is complex, involving both genetic and environmental factors. The serum level of IFNα in SLE has been shown to correlate with the severity of the disease (Dall'era et al. Ann Rheum Dis 2005; 64:1692-7). Sjögren's syndrome (SS), also known as sicca syndrome, is a chronic, systemic, autoimmune condition which affects the exocrine glands, particularly the salivary and lachrymal glands. Elevated IFNα activity has also been observed in the serum of patients suffering from this disease. Finally, other conditions such as diabetes, rheumatoid arthritis, scleroderma, vasculitis and autoimmune thyroiditis have also been shown to be associated with high levels of IFNα.

Sedaghat et al. also recently suggested that type 1 IFN may play a role in CD4$^+$ T cells depletion in HIV$^+$ patients as they showed that type 1 IFN affect the steady state of normal CD4$^+$ T cells dynamics by shifting the balance towards Th1 effectors that are short lived cells instead of long-lived memory T cells (Sedaghat et al. J. Virol. 2008, 82(4): 1870-1883). This was confirmed in Mandl et al., where it is suggested to diminish the IFNα production by plasmacytoid dendritic cells to ameliorate the pathological immune activation (Mandl et al. Nat. Med. 2008).

Moreover, administration of IFNα has been reported to exacerbate underlying disease in patients with psoriasis, autoimmune thyroiditis and multiple sclerosis and to induce an SLE like syndrome in patients without a previous history of autoimmune disease.

Therefore, there is a need for an agent that inhibits IFNα activity.

Passive immunization with monoclonal neutralizing antibodies is currently being tested in clinical trials with rontalizumab and sifalimumab for the treatment of SLE. However, said therapy presents the drawbacks of targeting only one subset of the 13 for IFNα and the use of passively administrated monoclonal antibodies can be limited by the induction of anti-drug antibodies. Said anti-drug antibodies may neutralize or otherwise compromise the clinical effect of the drugs and can also be associated with serious adverse events related to cross-reactivity with autologous proteins (De Groot et al. Trends. Immunol. 2007, 28(11)).

The present invention thus provides a method for inhibiting IFNα activity in vivo by administering a therapeutically effective amount of an immunogenic product that allows an active immunization which can break immunological B cell tolerance and generate high titers of polyclonal neutralizing antibodies against IFNα and its use for treating IFNα related conditions.

SUMMARY

One object of the invention is an immunogenic product comprising IFNα coupled to a carrier protein molecule for use in preventing or treating an IFNα related condition in a subject in need thereof, wherein the therapeutically effective amount of the immunogenic product to be administrated to the subject is more than 30 mcg of immunogenic product per administration, preferably at least 60 mcg.

In one embodiment of the invention, the administration of the therapeutically effective amount of the immunogenic product prevents the occurrence of symptoms of a disease linked to an over-production of IFNα.

In another embodiment of the invention, the administration of the therapeutically effective amount of the immunogenic product prevents the flare of a disease linked to an over-production of IFNα.

In another embodiment of the invention, the IFNα related conditions comprise systemic lupus erythematosus, rheumatoid arthritis, scleroderma, Sjögren syndrome, vasculitis, HIV, type I diabetes, autoimmune thyroiditis and myositis.

In another embodiment of the invention, the therapeutically effective amount of the immunogenic product to be administrated to the subject is from 35 mcg to 1000 mcg of immunogenic product per administration, preferably from 60 mcg to 1000 mcg.

In another embodiment of the invention, the immunogenic product is administrated to the subject at least twice in a month.

In another embodiment of the invention, the immunogenic product is further administrated to the subject at least once every three months.

In another embodiment of the invention, the immunogenic product is further administrated to the subject when, in a serum sample obtained from the subject, the amount of anti-IFNα antibodies is undetectable.

In another embodiment of the invention, the immunogenic product is strongly inactivated, which means that the product shows less than 5% of antiviral activity in the conditions of TEST B.

In another embodiment of the invention, the immunogenic product is capable of neutralizing the antiviral activity of IFNα in the conditions of TEST C.

In another embodiment of the invention, the immunogenic product comprises at least one subtype of IFNα.

In another embodiment of the invention, the subtype of IFNα is IFNα 2b and the carrier protein molecule is KLH.

In another embodiment of the invention, the immunogenic product is a vaccine, preferably in the form of an emulsion.

Another object of the invention is a unit dosage form comprising more than 30 mcg of an immunogenic product comprising IFNα coupled to a carrier protein molecule as defined here above.

Another object of the invention is a medical device comprising more than 30 mcg of an immunogenic product comprising IFNα coupled to a carrier protein molecule as defined here above.

Another object of the invention is a kit comprising at least one vial containing more than 30 mcg, preferably at least 60 mcg, of an immunogenic product comprising IFNα coupled to a carrier protein molecule as defined here above, at least one vial containing adjuvant, and means for contacting said immunogenic product to the adjuvant, and for emulsifying the mixture of the aqueous solution with the adjuvant.

In one embodiment, the kit of the invention comprises

- at least one vial containing more than 30 mcg, preferably at last 60 mcg, of an immunogenic product comprising IFNα coupled to a carrier protein molecule according to the invention, and means for solubilizing said immunogenic product, preferably in an aqueous solution, or
- at least one vial containing a solution preferably an aqueous solution, comprising more than 30 mcg, preferably at least 60 mcg, of an immunogenic product comprising IFNα coupled to a carrier protein molecule according to the invention, and
- at least one vial containing adjuvant, and means for contacting said solution to the adjuvant, and for emulsifying the mixture of the solution with the adjuvant.

Definitions

As used herein, the term "interferon α" or "IFNα" refers to IFN alpha proteins encoded by a functional gene of the interferon alpha gene locus with 75% or greater sequence identity to IFN alpha 1 (Genbank number NP_076918 or protein encoded by Genbank number NM_024013). Examples of human IFN alpha subtypes include IFN alpha 1 (Genbank number NP_076918), alpha 2a (Genbank number ITF_A), alpha 2b (Genbank number AAP20099), alpha 4 (Genbank number NP_066546), alpha 5 (Genbank number P01569), alpha 6 (P05013), alpha 7 (Genbank number P01567), alpha 8 (Genbank number P32881), alpha 10 (Genbank number P01566), alpha 14 (Genbank number P01570), alpha 16 (Genbank number NP_002164), alpha 17 (Genbank number P01571) and alpha 21 (Genbank number NP_002166). Examples of nonhuman mammal IFNα subtype may be found in Genbank as well known by the person skilled in the art (for review see Pestka et al Immunological reviews 2004, 202:8-32).

As used herein, the term "immune response" refers to the action, for example of lymphocytes, antigen presenting cells, phagocytic cells and macromolecules produced by the above cells or the liver (including antibodies, cytokines and complement).

As used herein, an antibody that "inhibits the biological activity" or "neutralizes the biological activity" of IFNα is intended to refer to an antibody that inhibits the activity of that cytokine by at least 10%, 20%, 30%, 40%, 50%, 60%, 70%, or 80% or more, as compared to the level of activity of the cytokine in the absence of the antibody, for example by using a functional assay such as those described in the Examples.

As used herein, the term "carrier protein molecule" refers to a protein or a peptide of at least 15 amino acids long which, when partially covalently being associated to the IFNα molecule for forming heterocomplexes, allows for a large number of antigens of IFNα to be presented to the B lymphocytes.

As used herein, the term "subject" includes any human or nonhuman mammals such as primates, dogs, cats, horses, sheep . . . .

As used herein, the term "patient" refers to a subject that is affected by an IFNα related condition.

As used herein, the term "effective amount" refers to an amount sufficient to cause a beneficial or desired clinical result (e.g. improvement in clinical condition).

As used herein, the term "treatment" or "treating" refers to clinical intervention in an attempt to alter the natural course of a disease of the subject or patient to be treated, and may be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, lowering the rate of disease progression, ameliorating or palliating the disease state, and causing remission, maintaining remission state or improved prognosis.

DETAILED DESCRIPTION

Although regulators of IFNα occur naturally in the body, their capacity to regulate the cytokine levels in diseases such as SLE and SS appears to be insufficient. The aim of the anti-IFNα therapeutic immunization of the invention is to raise antibody levels against the cytokine, while enhancing their affinity and neutralizing activity, resulting in the reduction of the excess cytokine and inhibiting its pathogenic effects, without interfering with other metabolic and physiological processes.

One object of the present invention is a method for treating an IFNα related condition in a subject in need thereof, comprising administering to the subject a therapeutically effective amount of an immunogenic product comprising IFNα coupled to a carrier protein molecule, wherein said therapeutically effective amount is more than 30 mcg (μg) of immunogenic product per administration.

In one embodiment of the invention, said therapeutically effective amount is at least 60 mcg (μg) of immunogenic product per administration.

In one embodiment of the invention, the therapeutically effective amount of the immunogenic product per administration is from more than 30 mcg, preferably more than 60 mcg to 1000 mcg. In another embodiment of the invention, the therapeutically effective amount of the immunogenic product per administration is from more than 30 mcg, preferably more than 60 mcg to 750 mcg. In another embodiment of the invention, the therapeutically effective amount of the immunogenic product per administration is from more than 30 mcg, preferably more than 60 mcg to 500 mcg. In another embodiment of the invention, the therapeutically effective amount of the immunogenic product per administration is from more than 30 mcg, preferably more than 60 mcg to 450 mcg. In another embodiment of the invention, the therapeutically effective amount of the immunogenic product per administration is from more than 30 mcg, preferably more than 60 mcg to 400 mcg. In another embodiment of the invention, the therapeutically effective amount of the immunogenic product per administration is from more than 30 mcg, preferably more than 60 mcg to 350 mcg. In another embodiment of the invention, the therapeutically effective amount of the immunogenic product per administration is from more than 30 mcg, preferably more than 60 mcg to 300 mcg. In another embodiment of the invention, the therapeutically effective amount of the immunogenic product per administration is from more than 30 mcg, preferably more than 60 mcg to 250 mcg. In another embodiment of the invention, the therapeutically effective amount of the immunogenic product per administration is from more than 30 mcg, preferably more than 60 mcg to 200 mcg. In another embodiment of the invention, the therapeutically effective amount of the immunogenic product per administration is from more than 30 mcg, preferably more than 60 mcg to 150 mcg. In another embodiment of the invention, the therapeutically effective amount of the immunogenic product per administration is from more than 30 mcg, preferably more than 60 mcg to 100 mcg.

In another embodiment of the invention, the therapeutically effective amount of the immunogenic product per administration is from 35 mcg to 1000 mcg. In another embodiment of the invention, the therapeutically effective amount of the immunogenic product per administration is from 35 mcg to 750 mcg. In another embodiment of the invention, the therapeutically effective amount of the immunogenic product per administration is from 35 mcg to 500 mcg. In another embodiment of the invention, the therapeutically effective amount of the immunogenic product per administration is from 35 mcg to 450 mcg. In another embodiment of the invention, the therapeutically effective amount of the immunogenic product per administration is from 35 mcg to 400 mcg. In another embodiment of the invention, the therapeutically effective amount of the immunogenic product per administration is from 35 mcg to 350 mcg. In another embodiment of the invention, the therapeutically effective amount of the immunogenic product per administration is from 35 mcg to 300 mcg. In another embodiment of the invention, the therapeutically effective amount of the immunogenic product per administration is from 35 mcg to 250 mcg. In another embodiment of the invention, the therapeutically effective amount of the immunogenic product per administration is from 35 mcg to 200 mcg. In another embodiment of the invention, the therapeutically effective amount of the immunogenic product per administration is from 35 mcg to 150 mcg. In another embodiment of the invention, the therapeutically effective amount of the immunogenic product per administration is from 35 mcg to 100 mcg.

In another embodiment of the invention, the therapeutically effective amount of the immunogenic product per administration is from 60 mcg to 1000 mcg. In another embodiment of the invention, the therapeutically effective amount of the immunogenic product per administration is from 60 mcg to 750 mcg. In another embodiment of the invention, the therapeutically effective amount of the immunogenic product per administration is from 60 mcg to 500 mcg. In another embodiment of the invention, the therapeutically effective amount of the immunogenic product per administration is from 60 mcg to 450 mcg. In another embodiment of the invention, the therapeutically effective amount of the immunogenic product per administration is from 60 mcg to 400 mcg. In another embodiment of the invention, the therapeutically effective amount of the immunogenic product per administration is from 60 mcg to 350 mcg. In another embodiment of the invention, the therapeutically effective amount of the immunogenic product per administration is from 60 mcg to 300 mcg. In another embodiment of the invention, the therapeutically effective amount of the immunogenic product per administration is from 60 mcg to 250 mcg. In another embodiment of the invention, the therapeutically effective amount of the immunogenic product per administration is from 60 mcg to 240 mcg. In another embodiment of the invention, the therapeutically effective amount of the immunogenic product per administration is from 60 mcg to 200 mcg. In another embodiment of the invention, the therapeutically effective amount of the immunogenic product per administration is from 60 mcg to 150 mcg. In another embodiment of the invention, the therapeutically effective amount of the immunogenic product per administration is from 60 mcg to 120 mcg. In another embodiment of the invention, the therapeutically effective amount of the immunogenic product per administration is from 60 mcg to 100 mcg.

In another embodiment of the invention, the therapeutically effective amount of the immunogenic product per administration is from 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390 mcg to 400 mcg.

In another embodiment of the invention, the therapeutically effective amount of the immunogenic product per administration is from 60 mcg to 240 mcg. In another embodiment of the invention, the therapeutically effective amount of the immunogenic product per administration is 60 mcg. In another embodiment of the invention, the therapeutically effective amount of the immunogenic product per administration is 120 mcg. In another embodiment of the invention, the therapeutically effective amount of the immunogenic product per administration is 240 mcg.

In one embodiment, the therapeutically effective amount corresponds to an amount of total proteins determined using a Bradford protein assay as well known in the art.

In one embodiment of the invention, the subject to be treated is administrated at least twice in a month with the therapeutically effective amount of immunogenic product as described here above.

In another embodiment of the invention, the subject to be treated is administrated two times in 1 month with the therapeutically effective amount of immunogenic product as described here above. In this embodiment, the subject may be administrated once at day 0 and the second time between day 7 and day 28. In another embodiment, the subject may be administrated once at day 0 and the second time between day 7 and day 21. In one embodiment, the subject is administrated once at day 0 and the second time at day 28.

In another embodiment of the invention, the subject to be treated is administrated three times in 1 month with the therapeutically effective amount of immunogenic product as described here above. In this embodiment, the subject to be treated may be administrated once at day 0, the second time between day 7 and day 14 and the third time between day 21 and day 28. In one embodiment, the subject is administrated once at day 0, the second time at day 7 and the third time at day 28.

In another embodiment of the invention, the subject to be treated is administered four times in 3 months with the therapeutically effective amount of immunogenic product as described here above. In this embodiment, the subject to be treated may be administered one at day 0, the second time between day 7 and day 14, the third time between day 21 and day 28 and the fourth time between day 77 and day 84. In one embodiment, the subject is administered once at day 0, the second time at day 7, the third time at day 28 and the fourth time at day 84.

In another embodiment of the invention, the subject to be treated may be further administrated once every three months with the therapeutically effective amount of the immunogenic product as described here above.

In one embodiment of the invention, the subject to be treated is administered three times in one month as described here above, and then further administered once every three months with the therapeutically effective amount of the immunogenic product as described here above.

In one embodiment of the invention, the subject to be treated is administered four times in three month as described here above, and then further administered once every three months with the therapeutically effective amount of the immunogenic product as described here above.

In another embodiment of the invention, the subject to be treated may be further administrated once every six months with the therapeutically effective amount of the immunogenic product as described here above.

In one embodiment of the invention, the subject to be treated is administered three times in one month or four times in three month as described here above, and then further administered once every six months with the therapeutically effective amount of the immunogenic product as described here above.

In another embodiment of the invention, the subject to be treated may be further administrated once a year with the therapeutically effective amount of the immunogenic product as described here above.

In one embodiment of the invention, the subject to be treated is administered three times in one month or four times in three month as described here above, and then further administered once every year with the therapeutically effective amount of the immunogenic product as described here above.

In another embodiment of the invention, the subject to be treated may be further administrated once every 5 years with the therapeutically effective amount of the immunogenic product as described here above.

In one embodiment of the invention, the subject to be treated is administered three times in one month or four times in three month as described here above, and then further administered once every 5 years with the therapeutically effective amount of the immunogenic product as described here above.

In another embodiment of the invention, the subject to be treated may be further administrated once every 10 years with the therapeutically effective amount of the immunogenic product as described here above.

In one embodiment of the invention, the subject to be treated is administered three times in one month or four times in three month as described here above, and then further administered once every 10 years with the therapeutically effective amount of the immunogenic product as described here above.

In another embodiment of the invention, the subject to be treated may be further administrated with the therapeutically effective amount of the immunogenic product as described here above when the amount of antibodies against IFNα is undetectable in a serum sample obtained from the subject.

In one embodiment of the invention, the subject to be treated is administered three times in one month or four times in three month as described here above, and then further administered with the therapeutically effective amount of the immunogenic product as described here above when the amount of antibodies against IFNα is undetectable in a serum sample obtained from the subject.

Quantification of the amount of antibodies against IFNα in a serum sample may be carried out by conventional methods known in the art, such as an ELISA anti-IFN.

One example of carrying out such method is the following:

coating a 96 wells plate with 100 ng of the subtype of IFNα used for preparing the immunogenic product such as IFNα-2b and incubate the plate overnight at 2° C.-8° C., blocking the plate with a blocking buffer during 90 min at 37° C., incubating the plate with the serum sample and pool of naïve sample during 90 min at 37° C.: the serum sample is typically diluted in a two fold dilution series starting from dilution 200× to at least 8 dilutions, incubating the plate with the labeled secondary antibody such as a goat anti-human immunoglobulin conjugated to HRP, developing the complex with an o-phenylenediamine dihydrochloride (OPD) substrate solution. After stopping the enzymatic reaction, the intensity of the resulting color is determined by spectrophotometric methods at 492 nm.

The anti-IFN titer for each sample is expressed as the minimal dilution for which the mean OD value is higher than the cut-off value:

Cut-off value=Mean OD of the pool of naive serum× 2.08 where the N cut-off value is equal to 2.08.

Then, the anti-IFN titer for each sample will be expressed as the minimal dilution for which the mean OD value is higher than the cut-off value. The first dilution being 200, patients are considered negative if their OD at ½₀₀ is inferior to the cut-off value (Mire-Sluis et al. 2004 J. Immunol. Meth. 289: 1-16).

In one embodiment of the invention, the subject to be treated is suffering from an IFNα related condition.

In another embodiment of the invention, the subject to be treated presents undetectable amount of anti-IFNα antibodies in the serum.

[Mechanism of Action]

The present invention also relates to an immunogenic product that is useful for inducing an immune response in a mammal to whom said immunogenic product is administered, including a humoral immune response wherein antibodies that neutralize the immunosuppressive, apoptotic or angiogenic properties of the endogenous cytokine IFNα.

The present invention also relates to a method for inducing an immune response in a mammal in need thereof, said method comprising the administration of an immunogenic product as hereinabove described to said mammal. In one embodiment, said immune response includes a humoral immune response wherein antibodies that neutralize the immunosuppressive, apoptotic or angiogenic properties of the endogenous cytokine are induced.

In one embodiment of the invention, the immunogenic product is an inactivated but immunogenic cytokine derivative of IFNα chemically coupled to a T-helper stimulating foreign carrier protein such as for example KLH. Said immunogenic product has the ability to disrupt B cell but not T cell tolerance to IFNα. Helper T cell tolerance against self is circumvented by linking IFNα to the foreign carrier protein.

B cells specific for IFNα are activated following antigen binding and endocytose the immunogenic product and carrier specific peptides are presented via the Major Histocompatibility Complex (MHC) class II molecules. This activation signal is not sufficient to induce B cell differentiation in the case of a T dependent antigen but because B cells process the self and the carrier antigens, T cell help can be given by T cells specific for the self or the carrier protein. Since T cell selection is very stringent, there is no specific T cell activation for the self antigen.

Dendritic cells (DC) can also take up the self antigen and the carrier molecule and present carrier specific peptides via their MHC class II molecules. DCs are thus able to activate naïve T helper cells specific for the carrier. The T helper cells are in turn able to provide carrier-specific T helper cells to B cells specific for the self antigen and to present carrier peptides on their MHC class II molecules.

T helper cells specific for the carrier interact with B cells specific for the self antigen, eliciting a normal antibody response against the self antigen.

The immunogenic product is mainly used in vaccine compositions for treating a disease linked to an over-production of IFNα.

More specifically, this invention relates to a method for treating a disease linked to an over-production of IFNα comprising a step of administering to the subject, a therapeutically effective amount of the immunogenic product of the invention.

This invention also relates to a method for treating a disease linked to an over-production of IFNα comprising the administration of a therapeutically effective amount of the immunogenic product, wherein the administration of the immunogenic product prevents the occurrence of symptoms of the disease.

The invention also relates to a method for treating a disease linked to an over-production of IFNα comprising the administration of a therapeutically effective amount of the immunogenic product, wherein the administration of the immunogenic product prevents the flare of the disease.

The invention also relates to a method for treating a disease linked to an over-production of IFNα comprising the administration of a therapeutically effective amount of the immunogenic product, wherein the administration of the immunogenic product induces the production of antibodies that neutralize the activity of endogeneous IFNα.

The invention also relates to a method for treating a disease linked to an over-production of IFNα comprising the administration of a therapeutically effective amount of the immunogenic product, wherein the administration of the immunogenic product induces the neutralization of the activity of endogeneous IFNα.

Examples of disease linked to an over-production of IFNα include, but are not limited to systemic lupus erythematosus, rheumatoid arthritis, scleroderma, Sjögren syndrome, vasculitis, HIV, type I diabetes, autoimmune thyroiditis and myositis.

A further object of the invention consists of a method for inducing the production of antibodies that neutralize the activity of endogeneous IFNα in a subject, comprising a step of administering to said subject a therapeutically effective amount of the immunogenic product.

[The Immunogenic Product]

The immunogenic product as used in the invention comprises IFNα coupled to a carrier protein molecule such as KLH, wherein the immunogenic product is inactivated.

The immunogenic product as used in the invention is a complex between at least one recombinant IFNα subtype and at least one carrier protein molecule such as for example KLH obtained by conjugation with glutaraldehyde and subsequent inactivation with formaldehyde.

In one embodiment of the invention, the carrier protein molecule may be any carrier molecule conventionally used in immunology such as KLH (Keyhole limpet hemocyanin), ovalbumin, bovine serum albumin (BSA), toxoid tetanos, toxoid diphteric B cholera toxin, mutant non toxic diphtheria toxin (CRM197), *neisseria meningitidis* outer membrane protein in outer membrane vesicles, non-typeable *Haemophilus influenza* outer membrane protein, *pseudomonas aeruginosa* toxin A, virus like particle (VLP) . . . . In one preferred embodiment, said carrier is KLH. Preferably, the KLH starting product consists of a highly purified KLH extracted from the lymph of the marine gastropod mollusk *Megathura cremulata*. Naturally produced KLH generally consists of a di-decamer structure which is a non covalent tubular assembly of 20 subunits.

In another embodiment of the invention, the recombinant IFNα subtype may be any subtype among IFN alpha 1, alpha 2a, alpha 2b, alpha 4, alpha 5, alpha 6, alpha 7, alpha 8, alpha 10, alpha 14, alpha 16, alpha 17 and alpha 21.

Recombinant IFNα subtypes may be obtained by conventional methods known in the art using the sequences from Genbank as described here above. For example, production of the recombinant IFNα subtype may be carried out by culturing cells containing an expression vector comprising the gene of the IFNα subtype and then harvesting the inclusion bodies and finally purifying the IFNα subtype.

In one embodiment of the invention, the recombinant IFNα subtype is the IFNα 2b subtype.

In one embodiment of the invention, the immunogenic product comprises at least the IFNα 2b subtype.

In one embodiment of the invention, the recombinant IFNα subtype is in a liquid solution, preferably a buffer solution having a pH ranging from 3.5, preferably from 6 to 7.8.

In one embodiment, when the subject to be treated is a human, the recombinant IFNα used is human.

In one embodiment of the invention, the immunogenic product comprises IFNα coupled to a carrier protein molecule such as for example KLH, wherein said immunogenic product is recognized by an anti-IFNα antibody.

The recognition of the immunogenic product by an anti-IFNα antibody may be carried out by conventional methods known in the art such as a sandwich ELISA anti-IFNα/carrier protein. The ELISA (TEST D) are developed by any colorimetric means known in the art such as for example using detection antibody labelled with biotin, a poly-streptavidin HRP amplification system and an o-phenylenediamine dihydrochloride substrate solution.

One example of said method is the following:
coating a plate with the capture antibody, such as for example a rabbit polyclonal anti-KLH antibody,
blocking the plate with a blocking buffer (such as casein 2% in PBS for example) during 90 min at 37° C.,
incubating during 90 min at 37° C. the plate with a dilution series of the immunogenic product from 250 ng/ml to 8 two fold dilutions or with negative controls such as KLH and IFNα,
incubating 90 min at 37° C. the plate with the detection antibody such as for example a biotinylated anti-IFNα antibody,
incubating the plate with streptavidin-HRP during 30 min at 37° C. and developing the complex with an o-phenylenediamine dihydrochloride (OPD) substrate solution furring 30 min. After stopping the enzymatic reaction, the intensity of the resulting color is determined by spectrophotometric methods at 490 nm.

When optical density of wells containing the immunogenic product is at least 10 times superior to the optical density of wells containing the negative control, the person skilled in the art considers that the immunogenic product is recognized by an anti-IFNα antibody and that IFNα in the immunogenic product is coupled to the KLH.

In another embodiment of the invention, the immunogenic product comprises IFNα coupled to a carrier protein molecule such as for example KLH, wherein said immunogenic product is strongly immunogenic, which means that the product is capable of inducing antibodies anti-IFNα in vivo in the conditions of hereunder tested TEST A.

Test A is carried out according to the following method: 0.3 to 10 µg of total proteins (as determined by a Bradford protein assay) of the immunogenic product is injected in Balb/c mice of 6-8 weeks twice in 30 days, preferably at day 0 and day 21. A serum sample is obtained before immunization (pre-immune serum sample) and between day 30 and day 40 (test serum sample), preferably at day 31. An ELISA anti-IFNα is carried out as explained here above.

Briefly, a 96 wells plate is coated with 100 ng of the subtype of IFNα used for preparing the immunogenic product such as IFNα-2b and incubated overnight at 2° C.-8° C. The plate is then blocked with a blocking buffer during 90 min at 37° C. 100 µl of pre-immune sample at dilution 1/2500 and a dilution series from 1/2500 up to 8 two fold dilutions of the serum samples (pre-immune and test) are added to the wells. An anti-mouse immunoglobulins labeled secondary antibody such as an HRP conjugated antibody is finally added to the wells and the ELISA is developed using any colorimetric means known in the art such as for example an o-phenylenediamine dihydrochloride substrate solution.

When optical density of wells containing the test serum sample is at least 2 times superior to the optical density of wells containing the pre-immune serum sample, the person skilled in the art considers that the immunogenic product is immunogenic, which means that it had induced anti-IFNα antibodies in vivo.

In another embodiment of the invention, the immunogenic product comprises IFNα coupled to a carrier protein molecule such as for example KLH, wherein the IFNα is strongly inactivated, which means that the product shows less than 5%, preferably less than 1% of antiviral activity of IFNα in the conditions of hereunder cited TEST B. In one embodiment, the immunogenic product of the invention at a concentration of 500 ng/mL or more shows less than 5%, preferably less than 1% of antiviral activity of IFNα at a concentration of 500 ng/mL or more in the conditions of TEST B.

This assay is based on the protective effect of IFNα on the cytopathic effect (CPE) of Vesicular Stomatitis Virus (VSV) on Madin-Darby Bovine Kidney (MDBK) cells. This assay may also be carried out using Hep-2C or A549 human cells and EMCV virus.

Test B is carried out according to the following method:

The immunogenic product and the recombinant IFNα subtype used for preparing the immunogenic product (positive control) are diluted at at least 500 ng/ml and at least 1000 U/ml respectively in Basal medium (RPMI supplemented with 2 mM glutamine, 1 mM sodium pyruvate, 1 mM Hepes). 50 µl of the immunogenic product and the positive control are plated in a 96 wells plate and diluted in a series of two fold dilutions in the Basal medium. $2 \cdot 10^4$ MDBK cells are added in each well in 50 µl of Cell medium (RPMI supplemented with 4% FBS, 2 mM glutamine, 1 mM sodium pyruvate and 1 mM Hepes) and the plate is incubated overnight at 37° C., 5% $CO_2$. The virus is then diluted in Basal medium to at least 10 $TCID_{50}$ (Tissue Culture Infection Dose 50: 10 times the dilution to kill 50% of infected cells). The plate is emptied and 100 µl of the diluted virus is added. The plate is then incubated overnight at 37° C., 5% $CO_2$.

At the end of the culture, viability of the MDBK cells is assessed using methods well-known in the art. One example of said methods is the following: 20 µl/well of a solution of MTS/PMS (100 µl MTS/5 ti PMS; Promega G5430) are added to the wells and the plate is incubated for another 4 h at 37° C. 5% CO2. The plate is then read at 490 nm on a spectrophotometer.

The percentage of antiviral activity is calculated as following:

% antiviral activity=[($OD_{product}$−$OD_{virus}$)/mean $OD_{cells}$−$OD_{virus}$)]*100

$OD_{product}$ stands for the optical density of well with the immunogenic product or with the positive control (IFNα subtype).

$OD_{virus}$ stands for the optical density of control well with the virus only.

$OD_{cells}$ stands for the optical density of control well with IFNα and virus.

The $EC_{50}$ value, corresponding to the amount of immunogenic product resulting in 50% inhibition of virus-mediated mortality, is determined by interpolating the $EC_{50}$ value onto the x axis on a viability/concentration graph.

Comparing the $EC_{50}$ of the immunogenic product and the $EC_{50}$ of the positive control (the recombinant IFNα subtype used for preparing the immunogenic product) allows determining whether the immunogenic product shows less than 5%, preferably less than 1% of antiviral activity.

An Inactivation Factor $EC_{50\ product}/EC_{50\ IFN\alpha}$ can be calculated: when the immunogenic product shows less than 5%, preferably less than 1% of antiviral activity, the Inactivation Factor is more than 20, preferably more than 100.

In another embodiment of the invention, the immunogenic product comprises IFNα coupled to a carrier protein molecule such as for example KLH, wherein the immunogenic product is capable of neutralizing the antiviral activity of IFNα in the conditions of hereunder cited TEST C. According to the invention, this assay is performed to evaluate the neutralizing capacity of the serum obtained from mice immunized with the immunogenic product. The neutralizing capacity may be assessed by evaluating the cell viability in presence of the vesicular stomatitis virus replicating in MDBK cells. This assay may also be carried out using Hep-2C human cells and EMCV virus.

Test C is carried out according to the following method:

0.3 to 10 µg of total proteins (as determined by a Bradford protein assay) of the immunogenic product is injected in Balb/c mice of 6-8 weeks twice in 30 days, preferably at day 0 and day 21. A serum sample is obtained before immunization (pre-immune serum sample) and between day 30 and day 40 (test serum sample), preferably at day 31.

25 µl of pre-immune and test serum samples are plated in a 96-well plate at a dilution of 1/200 up to 8 dilutions from 1/200. The positive control (polyclonal anti-IFNα from PBL, Piscataway, N.J., ref. 31100-1) is typically diluted to be able to neutralize IFNα activity from 3125 UI/well to 100 UI/well in Basal medium (RPMI supplemented with 2 mM glutamine, 1 mM sodium pyruvate and 1 mM hepes) and 25 µl were also plated in the plate.

25 U/well (final concentration) in 25 µl of basal medium of IFNα is added to each well and the plate is incubated for 60 min at room temperature.

20000 MDBK cells in Assay medium (RPMI supplemented with 4% FBS, 2 mM glutamine, 1 mM sodium pyruvate, 1 mM hepes) are added to each well and the plate is incubated overnight at 37° C., 5% $CO_2$.

The virus is diluted to at least 10 $TCID_{50}$ (10 times the dilution to kill 50% of infected cells) in virus medium (RPMI supplemented with 2 mM glutamine, 1 mM sodium pyruvate, 1 mM hepes). The plate is emptied and 100 μl of virus is added to each well before incubation for 24 h at 37° C., 5% $CO_2$.

At the end of the culture, viability of the MBDK cells is assessed using methods well-known in the art. One example of said methods is the following: 20 μl/well of a solution of MTS/PMS (100 μl MTS/5 μl PMS; Promega G5430) are added to the wells and the plate is incubated for another 4 h at 37° C. 5% CO2. The plate is then read at 490 nm on a spectrophotometer.

The relative cell viability is calculated as following:

$$\% = [(OD_{sample} - OD_{virus})/OD_{IFN+virus}]*100$$

$OD_{sample}$ stands for the optical density of well with the serum obtained from the mouse immunized with the immunogenic product or with the positive control (polyclonal anti-IFN antibody).

$OD_{virus}$ stands for the optical density of control well with the virus only.

$OD_{IFN+virus}$ stands for the optical density of control well with IFNα and virus.

The $NC_{50}$ value, corresponding to the dilution of serum resulting in 50% neutralization of virus-mediated mortality expressed as a dilution factor or neutralizing unit/ml, is determined by interpolating the $NC_{50}$ value onto the x axis on a viability/concentration graph.

In TEST C, a result showing that the serum obtained from the mouse immunized with the immunogenic product does not protect the MBDK cells from mortality means that the immunogenic product has the capacity to induce antibodies directed against IFNα that neutralize its antiviral activity.

In one embodiment, the immunogenic product comprises IFNα coupled to a carrier protein molecule such as for example KLH, wherein the immunogenic product is capable of neutralizing at least 50% of the antiviral activity of IFNα in the conditions of TEST C. In said embodiment, the $NC_{50}$ can be calculated. If the dilution of serum is not capable of neutralizing at least 50% of the antiviral activity of IFNα in the conditions of TEST C, the $NC_{50}$ of the product cannot be calculated.

In one embodiment of the invention, the immunogenic product comprises IFNα coupled to a carrier protein molecule such as for example KLH, wherein the ratio IFNα/carrier in weight is ranging from 0.06 to 0.6.

In another embodiment of the invention, the immunogenic product comprises IFNα coupled to a carrier protein molecule such as for example KLH, wherein the ratio IFNα/carrier is 0.1 to 0.5.

In another embodiment of the invention, the immunogenic product comprises IFNα coupled to a carrier protein molecule such as for example KLH, wherein the ratio IFNα/carrier is 0.3.

In another embodiment of the invention, the immunogenic product comprises IFNα coupled to a carrier protein molecule such as for example KLH, wherein the ratio IFNα/carrier is 0.05, 0.1, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.5.

Said ratio may be calculated according to a method based on UV and fluorescence detection (Test E) as described in Example 10.

[Method for Obtaining the Immunogenic Product]

In one embodiment of the invention, the IFNα kinoid is obtained according to the following method:
  a) mixing together the at least one recombinant human IFNα subtype and the at least one carrier protein molecule with glutaraldehyde and blocking the reaction by adding a quenching compound selected from (i) a reducing agent and (ii) an amino acid selected from the group consisting of lysine and glycine and mixture thereof,
  b) removing compounds having a molecular weight of less than 10 kDa, or of less than 8 kDa
  c) adding formaldehyde;
  d) blocking the reaction with formaldehyde by adding a quenching compound selected from (i) a reducing agent and (ii) an amino acid selected from the group consisting of lysine and glycine and mixture thereof,
  e) collecting the said immunogenic product.

In one embodiment of step a), IFNα and the carrier protein molecule such as for example KLH are firstly mixed together in the appropriate amounts, before adding glutaraldehyde.

In one embodiment, IFN α and KLH are mixed at step a) at a IFNα:subunitKLH molar ratio ranging from 10:1 to 40:1. In another embodiment, IFN α and KLH are mixed at step a) at a IFN α:subunitKLH molar ratio ranging from 15:1 to 25:1. In another embodiment, IFN α and KLH are mixed at step a) at a IFN α:subunitKLH molar ratio ranging from 20:1 to 25:1.

In one embodiment of step a), glutaraldehyde is used at a final concentration in the reaction mixture ranging from 1 mM to 250 mM, preferably from 20 mM to 30 mM, more preferably from 22.5 mM to 25 mM. In one embodiment of step a), glutaraldehyde is incubated with IFN α and KLH for a period of time ranging from 15 min to 120 min, preferably about 30, 35, 40, 45, 50, 60, 70, 80, 90 minutes. In one embodiment, glutaraldehyde is added at 22.5 mM during about 45 minutes. Advantageously, step a) of incubation with glutaraldehyde is performed at a temperature ranging from 18° C. to 37° C., preferably from 18° C. to 27° C.

According to an embodiment, the reaction with glutaraldehyde (step a) is stopped prior to removing compounds having a molecular weight of less than 10 kDa, (step b) by adding a quenching compound, preferably a quenching compound that is selected from (i) a reducing agent and (ii) an amino acid selected from the group consisting of lysine and glycine and mixture thereof.

The reducing agent may consist of any one of the reducing agents known in the art which, due to their reducing properties, have the ability to reduce the remaining imine groupments generated during aldehyde treatment. The reducing agent may be selected from the group consisting of sodium borohydride, sodium cyanoborohydride.

According to an embodiment, in the embodiments wherein the said quenching compound is an amino acid, the said amino acid consists of glycine. In some embodiments of step b) where glycine and/or lysine are used for blocking the reaction with glutaraldehyde, the selected amino acid is used at a final concentration in the reaction mixture ranging from 0.01 M to 1 M, preferably from 0.05 M to 0.5 M, and most preferably from 0.08 M to 0.2 M, e.g. at 0.1 M as shown in the examples herein. In an embodiment, incubation with the quenching compound is performed for a period of time ranging from 1 minute to 120 minutes, preferably from 5 minutes to 60 minutes, e.g. for 30 minutes as shown in the examples herein. In another embodiment, this step is performed at a temperature ranging from 18° C. to 30° C., preferably from 18° C. to 25° C.

At step b), the small compounds of less than 10 kDa that are present in the reaction mixture are removed. These small compounds encompass mainly the excess glutaraldehyde and the excess quenching compound molecules that have not reacted with IFN α nor KLH. Step b) may be performed according to any known technique which allows removing compounds of less than 10 kDa, which techniques include dialysis with a dialysis membrane having a cut-off of 10 kDa or filtration using a filtration membrane having a cut-off of 10 kDa. Illustratively, step b) may consist of a step of tangential flow filtration using a filtration membrane having a cut-off of 10 kDa, as it is shown in the examples herein. The filtration retentate, which is devoid of the undesirable small compounds, is collected at the end of step b). If desired, step b) may comprise a preliminary step of removing the eventual compound aggregates present in the reaction mixture obtained at the end of step b). The said preliminary step may consist of a conventional filtration step for removing aggregates eventually present in suspension in a liquid solution, e.g. a filtration step using an appropriate filtration membrane, e.g. a filtration membrane having a pore size of 0.2 µm.

In one embodiment of step c) of the method, formaldehyde is added at a final concentration from 6 mM to 650 mM, preferably from 25 mM to 250 mM. In one embodiment of step c) of the method, formaldehyde is added for a period of time from 1 h to 336 hours, preferably from 1 h to 144 hours. In one embodiment, formaldehyde is applied at a final concentration of 50 to 100 mM, preferably 66 mM during 20 to 50 hours, preferably 40 hours.

At step c), incubation with formaldehyde is performed preferably at a temperature ranging from 30° C. to 40° C., e.g. at 37° C. as it is shown in the examples herein.

At step d) of the method, the reaction with formaldehyde is stopped by adding a quenching compound, preferably a quenching compound that is selected from (i) a reducing agent and (ii) an amino acid selected from the group consisting of lysine and glycine.

The reducing agent may consist in any one of the reducing agents known in the art which, due to their reducing properties, reduce the remaining imine groupements generated during aldehyde treatment. The reducing agent may be selected from the group consisting of sodium borohydride, sodium cyanoborohydride. According to an embodiment, in the embodiments wherein the said quenching compound is an amino acid, the said amino acid consists of glycine. In some embodiments of step b) where glycine and/or lysine are used for blocking the reaction with formaldehyde, the selected amino acid is used at a final concentration in the reaction mixture ranging from 0.01 M to 1.5 M, preferably from 0.05 M to 1 M, and most preferably from 0.1 M to 0.2 M, e.g. at 0.1 M as shown in the examples herein. In an embodiment, incubation with the quenching compound is performed for a period of time ranging from 5 minutes to 120 minutes, preferably from 10 minutes to 60 minutes, e.g. for 30 minutes as shown in the examples herein. In another embodiment, this step is performed at a temperature ranging from 18° C. to 30° C., preferably from 18° C. to 25° C.

According to one embodiment of the method, just prior to collecting at step e), removal of substances having a molecular weight of less than 100 kDa may be performed by the skilled artisan by any technique known in the art for removing substances having a molecular weight of more than 100 kDa from a liquid solution. In a first embodiment, the technique used is a filtration step that is performed by using a filtration membrane having a cut-off value of at least 100 kDa, which encompasses an ultrafiltration step or a tangential filtration step. In a second embodiment, the technique used consists of a tangential filtration step using a filtration membrane having a cut-off value of at least 100 kDa. In another embodiment, just prior to collecting at step e), removal of substances having a molecular weight of less than 300 kDa may be performed by using a filtration membrane having a cut-off value of at least 300 kDa.

[Composition, Emulsion and Vaccine Containing Such Emulsion]

This invention relates to a composition comprising the immunogenic product as described here above. This invention also relates to a formulation of the product of the invention, wherein the product is within an emulsion. Advantageously, the vaccine composition of the invention comprises or consists of said emulsion. Such emulsion comprises the immunogenic product of the invention, an oil and a surfactant or a mixture of at least one oil and at least one surfactant. Preferably, the oil or the mixture oil/surfactant is a pharmaceutically acceptable excipient. More preferably, the mixture of oil and surfactant is an adjuvant, even more preferably an immunoadjuvant. Preferred adjuvant is ISA 51. Another example of immunoadjuvant that may be used is SWE (squalene-based oil-in-water emulsion). Another example of immunoadjuvant that may be used is SWE-a (squalane-based oil-in-water emulsion). The emulsion of the invention may be a water-in-oil emulsion or an oil-in-water emulsion.

In another embodiment, the amount of the immunogenic product according to the invention is of more than 0.01% (w/w) and less than 1% (w/w) of the total weight of the said emulsion.

[Adjuvants]

The emulsion or the vaccine composition of the invention may comprise adjuvant, especially immunoadjuvants. In an embodiment, the amount of adjuvant ranges from 0.00001% (w/w) to 1%, preferably 0.0001 to 0.1%, more preferably from 0.001 to 0.01% (w/w) of the total weight of the vaccine composition.

Any suitable adjuvant known by the skilled artisan may be used in the vaccine composition above, including oil-based adjuvants such as for example Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), MPL (monophosphoryl lipid A), proteoglycans (e.g., extracted from *Klebsiella pneumoniae*), streptococcal preparations (e.g., OK432), Biostim™ (e.g., 01 K2), the "Iscoms" of EP 109 942, EP 180 564 and EP 231 039, aluminum hydroxide, saponin, DEAE-dextran, neutral oils (such as miglyol), vegetable oils (such as arachid oil), liposomes, Pluronic® polyols, the Ribi adjuvant system (see, for example GB-A-2 189 141), or interleukins, particularly those that stimulate cell mediated immunity. An alternative adjuvant consisting of extracts of *Amycolata*, a bacterial genus in the order Actinomycetales, has been described in U.S. Pat. No. 4,877,612. Alternatively, SWE (squalene 3.9%, span 0.47%, tween 80 0.47% in citrate buffer) and SWE-a (squalane 3.9%, span 0.47%, tween 80 0.47% in citrate buffer) may also be used. Additionally, proprietary adjuvant mixtures are commercially available. The adjuvant used will depend, in part, on the recipient organism. The amount of adjuvant to administer will depend on the type and size of animal. Optimal dosages may be readily determined by routine methods.

Oil adjuvants suitable for use in water-in-oil emulsions may include mineral oils and/or metabolizable oils. Mineral oils may be selected from BAYOL®, MARCOL®, and DRAKEOL®, including DRAKEOL® 6VR (SEPPIC, France). Metabolisable oils may be selected from SP oil (hereinafter described), Emulsigen (MPV Laboratories, Ralston, NZ), Montanide 264,266,26 (Seppic SA, Paris, France), as well as vegetable oils, such as peanut oil and soybean oil, animal oils such as the fish oils squalane and squalene, and tocopherol and its derivatives.

In addition, the adjuvant may include one or more wetting or dispersing agents in amounts of about 0.1 to 25%, more preferably about 1 to 10%, and even more preferably about 1 to 3% by volume of the adjuvant. Particularly preferred as wetting or dispersing agents are non-ionic surfactants. Useful non-ionic surfactants include polyoxyethylene/polyoxypropylene block copolymers, especially those marketed under the trademark PLURONIC®. and available from BASF Corporation (Mt. Olive, N.J.). Other useful nomome surfactants include polyoxyethylene esters such as polyoxyethylene sorbitan monooleate, available under the trademark TWEEN 80®, or mannide monooleate. It may be desirable to include more than one, e.g. at least two, wetting or dispersing agents in the adjuvant as part of the vaccine composition of the invention.

Suitable adjuvants may include but are not limited to surfactants known by one skilled in the art, such as for example hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," Sem. Hematol., 30:3-15 (1993).

[Further Surfactants]

In the embodiments of a vaccine composition according to the invention comprising an emulsion, the vaccine composition preferably contains, in addition to the combination of the immunogenic product and the one or more oily immunoadjuvant substances, also one or more surfactant agents. Illustrative embodiments of surfactive agents include mannide monoleate such as MONTANIDE® 80 marketed by Arlacel (SEPPIC, France).

In an embodiment, the amount of surfactant agent ranges from 0.00001% (w/w) to 1%, preferably 0.0001 to 0.1%, more preferably from 0.001 to 0.01% (w/w) of the total weight of the vaccine composition.

[Lyophilized Products]

According to an embodiment and for storage purposes, the product or the vaccine composition of the invention may be lyophilized. Vaccine compositions may thus be presented in a freeze-dried (lyophilized) form. In said embodiment, the immunogenic product according to the invention is combined with one or more lyophilisation auxiliary substances. Various lyophilisation auxiliary substances are well known by the one skilled in the art. Lyophilization of auxiliary substances encompasses sugars like lactose and mannitol.

In such embodiment where the vaccine composition consists of a lyophilised composition for use as a liquid emulsion comprising a surfactant agent, the vaccine composition preferably comprises an amount of the immunogenic product according to the invention of more than 0.1% (w/w) and less than 10% (w:w) of the total weight of the said vaccine composition.

[Stabilizers]

In some embodiments, the vaccine may be mixed with stabilizers, e.g. to protect degradation-prone proteins from being degraded, to enhance the shelf-life of the vaccine, or to improve freeze-drying efficiency. Useful stabilisers are i.a, SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, mixtures of amino acids such as lysine or glycine, and buffers, such as alkali metal phosphates.

[Administration Route]

The vaccine compositions according to the invention may be administered to the subject to be immunized by any conventional method including, by injectable, e.g. intradermal, intramuscular, intraperitoneal, or subcutaneous injection; or by topical, such as for example by transdermal delivery. The treatment may consist of a single dose or a plurality of doses over a period of time.

[Dosage Form]

The forms suitable for injectable use may include sterile solutions or dispersions and sterile powders for the extemporaneous preparation of sterile injectable solutions or dispersions. The prevention against contamination by microorganisms can be brought about by adding in the vaccine composition preservatives such as various antibacterial and antifungal agents, for example, parabens, chlorobutanol, phenol, sorbic acid, thimerosal and the like. In many cases, it may be preferable to include isotonic agents, for example, sugars or sodium chloride, for reduce pain during injection. Prolonged absorption of the injectable compositions can be brought about by the use in the compositions of agents delaying absorption, for example, aluminium monostearate and gelatine.

According to an embodiment, a lyophilized vaccine composition, of the invention is solubilized in water for injection and gently mixed; then an immunoadjuvant, preferably ISA 51, is added; the mixture is gently mixed for emulsification and charged into a suitable syringe. This invention thus also relates to a medical device, including a syringe filled or prefilled with a vaccine composition of the invention. The emulsion is ideally prepared extemporaneously. However, the syringe containing the emulsion can be stored less than 10 hours at 2-8° C. In this case, the emulsion should be allowed to warm up before injecting by friction between the hands.

[Unit Dosage Range]

Another object of the invention is a dosage unit comprising an amount of the immunogenic product ranging from more than 30 mcg to 1000 mcg. In another embodiment, the dosage unit comprises an amount of the immunogenic product ranging from 35 mcg to 1000 mcg. In another embodiment, the dosage unit comprises an amount of the immunogenic product ranging from 35 mcg to 750 mcg. In another embodiment, the dosage unit comprises an amount of the immunogenic product ranging from 35 mcg to 500 mcg. In another embodiment, the dosage unit comprises an amount of the immunogenic product ranging from 35 mcg to 450 mcg. In another embodiment, the dosage unit comprises an amount of the immunogenic product ranging from 35 mcg to 400 mcg. In another embodiment, the dosage unit comprises an amount of the immunogenic product ranging from 35 mcg to 350 mcg. In another embodiment, the dosage unit comprises an amount of the immunogenic product ranging from 35 mcg to 300 mcg. In another embodiment, the dosage unit comprises an amount of the immunogenic product ranging from 35 mcg to 250 mcg. In another embodiment of the invention, the therapeutically effective amount of the immunogenic product per administration is from 60 mcg to 1000 mcg. In another embodiment of the invention, the therapeutically effective amount of the immunogenic product per administration is from 60 mcg to 750 mcg. In another embodiment of the invention, the therapeutically effective amount of the immunogenic product per administration is from 60 mcg to 500 mcg. In another embodiment of the invention, the therapeutically effective amount of the immunogenic product per administration is from 60 mcg to 450 mcg. In another embodiment of the invention, the therapeutically effective amount of the immunogenic product per administration is from 60 mcg to 400 mcg. In another embodiment of the invention, the therapeutically effective amount of the immunogenic product per administration is from 60 mcg to 350 mcg. In another embodiment of the invention, the therapeutically effective amount of the immunogenic product per administration is from 60 mcg to 300 mcg. In another embodiment of the invention, the therapeutically effective amount of the immunogenic product per administration is from 60 mcg to 250 mcg. In another embodiment of the invention, the therapeutically effective amount of the immunogenic product per administration is from 60 mcg to 240 mcg. In another embodiment of the invention, the therapeutically effective amount of the immunogenic product per administration is from 60 mcg to 200 mcg. In another embodiment of the invention, the therapeutically effective amount of the immunogenic product per administration is from 60 mcg to 150 mcg. In another embodiment of the invention, the therapeutically effective amount of the immunogenic product per administration is from 60 mcg to 120 mcg. In another embodiment of the invention, the therapeutically effective amount of the immunogenic product per administration is from 60 mcg to 100 mcg. In another embodiment, the dosage unit comprises an amount of the immunogenic product ranging from 35, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390 to 400 mcg.

In another embodiment, the dosage unit comprises an amount of the immunogenic product ranging from 60 mcg to 240 mcg. In another embodiment, the dosage unit comprises an amount of the immunogenic product ranging from 60 mcg to 120 mcg.

In another embodiment, the dosage unit comprises an amount of the immunogenic product of 60 mcg. In another embodiment, the dosage unit comprises an amount of the immunogenic product of 120 mcg. In another embodiment, the dosage unit comprises an amount of the immunogenic product of 240 mcg.

[Kit and Medical Device]

This invention also pertains to a kit comprising:
1 vial (Vial Number 1) containing the immunogenic product of the invention, typically of 3 mL;
1 vial (Vial Number 2) containing adjuvant, preferably ISA51; this vial is capable of containing 3 mL of adjuvant and may be a container of 8 mL;
1 syringe, typically a Braun INJEKT-F® of 1 mL;
1 needle (Needle Number 1) for emulsion preparation; this needle is preferably a 20G needle;
1 needle (Needle Number 2) for injection, preferably intramuscular injection; this needle is preferably a 23G needle.

This invention also pertains to a method for preparing a vaccine from the kit, comprising:

(1) pulling up 0.4 ml of adjuvant from Vial Number 2. Discharge this syringe content into Vial Number 1 containing 0.4 ml of immunogenic product.
(4) pumping up and down the total vial content a sufficient number of times for emulsifying the content, typically 30 times and finally pulling up the whole emulsion.

Prior to injection, Needle Number 1 is preferably switched for Needle Number 2 and air is purged from the syringe.

In one embodiment, said kit comprises:
1 vial (Vial Number 1) containing 0.4 ml of the immunogenic product of the invention;
1 vial (Vial Number 2) containing at least 0.4 ml of adjuvant, preferably ISA51;
1 syringe, typically a Braun INJEKT-F® of 1 mL;
1 needle (Needle Number 1) for emulsion preparation; this needle is preferably a 20G needle;
1 needle (Needle Number 2) for injection, this needle is preferably a 23G needle.

In another embodiment, the immunogenic product is in a lyophilized form. Therefore, the kit comprises:
1 vial (Vial Number 1) containing lyophilized product of the invention, typically of 3 mL;
1 vial (Vial Number 2) containing water for injection typically of 2 mL;
1 vial (Vial Number 3) containing adjuvant, preferably ISA51; this vial is capable of containing 3 mL of adjuvant and may be a container of 8 mL;
1 syringe, typically a Braun Injekt-F® of 1 mL;
1 needle (Needle Number 1) for emulsion preparation; this needle is preferably a 20G needle;
1 needle (Needle Number 2) for injection, preferably intramuscular injection; this needle is preferably a 23G needle.

This invention also pertains to a method for preparing a vaccine from the kit, comprising:

(1) injecting of water for injection from Vial Number 2 into the Vial Number 1 by using the syringe connected to Needle number 1;
(2) rotating gently Vial Number 1 during 1-5 minutes until complete solubilization of the preparation;
(3) with the same syringe and needle, pulling up adjuvant from Vial Number 3. Discharge this syringe content into Vial Number 1.
(4) pumping up and down the total vial content a sufficient number of times for emulsifying the content, typically 30 times and finally pulling up the whole emulsion.

This invention also relates to the medical device which is the syringe filled or prefilled with the composition, emulsion or vaccine of the invention.

In one embodiment, said syringe is a dual chamber syringe, wherein one chamber comprises a solution with the immunogenic product of the invention and the other chamber comprises the adjuvant.

The invention also relates to a medical device comprising a vial or a carpule prefilled with the product of the invention or with the vaccine composition of the invention.

In one embodiment, the medical device comprises an amount of the immunogenic product ranging from more than 30 mcg to 1000 mcg. In another embodiment, the medical device comprises an amount of the immunogenic product ranging from 35 mcg to 1000 mcg. In another embodiment, the medical device comprises an amount of the immunogenic product ranging from 35 mcg to 750 mcg. In another embodiment, the medical device comprises an amount of the immunogenic product ranging from 35 mcg to 500 mcg. In another embodiment, the medical device comprises an amount of the immunogenic product ranging from 35 mcg to 450 mcg. In another embodiment, the medical device comprises an amount of the immunogenic product ranging from 35 mcg to 400 mcg. In another embodiment, the medical device comprises an amount of the immunogenic product ranging from 35 mcg to 350 mcg. In another embodiment, the medical device comprises an amount of the immunogenic product ranging from 35 mcg to 360 mcg. In another embodiment, the medical device comprises an amount of the immunogenic product ranging from 35 mcg to 250 mcg. In another embodiment of the invention, the therapeutically effective amount of the immunogenic product per administration is from 60 mcg to 1000 mcg. In another embodiment of the invention, the therapeutically effective amount of the immunogenic product per administration is from 60 mcg to 750 mcg. In another embodiment of the invention, the therapeutically effective amount of the immunogenic product per administration is from 60 mcg to 500 mcg. In another embodiment of the invention, the therapeutically effective amount of the immunogenic product per administration is from 60 mcg to 450 mcg. In another embodiment of the invention, the therapeutically effective amount of the immunogenic product per administration is from 60 mcg to 400 mcg. In another embodiment of the invention, the therapeutically effective amount of the immunogenic product per administration is from 60 mcg to 350 mcg. In another embodiment of the invention, the therapeutically effective amount of the immunogenic product per administration is from 60 mcg to 300 mcg. In another embodiment of the invention, the therapeutically effective amount of the immunogenic product per administration is from 60 mcg to 250 mcg. In another embodiment of the invention, the therapeutically effective amount of the immunogenic product per administration is from 60 mcg to 240 mcg. In another embodiment of the invention, the therapeutically effective amount of the immunogenic product per administration is from 60 mcg to 200 mcg. In another embodiment of the invention, the therapeutically effective amount of the immunogenic product per administration is from 60 mcg to 150 mcg. In another embodiment of the invention, the therapeutically effective amount of the immunogenic product per administration is from 60 mcg to 120 mcg. In another embodiment of the invention, the therapeutically effective amount of the immunogenic product per administration is from 60 mcg to 100 mcg. In another embodiment, the medical device comprises an amount of the immunogenic product ranging from 35, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390 to 400 mcg.

In another embodiment, the medical device comprises an amount of the immunogenic product ranging from 60 mcg to 240 mcg. In another embodiment, the medical device comprises an amount of the immunogenic product ranging from 60 mcg to 120 mcg.

In another embodiment, the medical device comprises an amount of the immunogenic product of 60 mcg. In another embodiment, the medical device comprises an amount of the immunogenic product of 120 mcg. In another embodiment, the medical device comprises an amount of the immunogenic product of 240 mcg.

EXAMPLES

Figure 1:
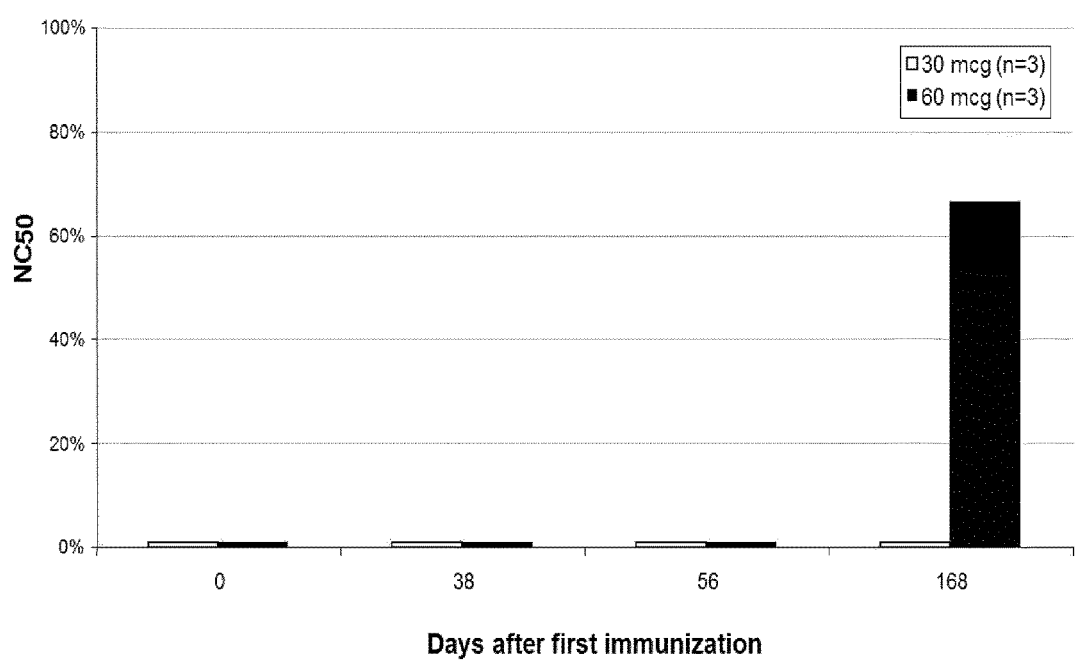
FIG. 1: Percentage of immunized patient serum samples showing IFNα neutralizing activity during interim report.
Figure 2:
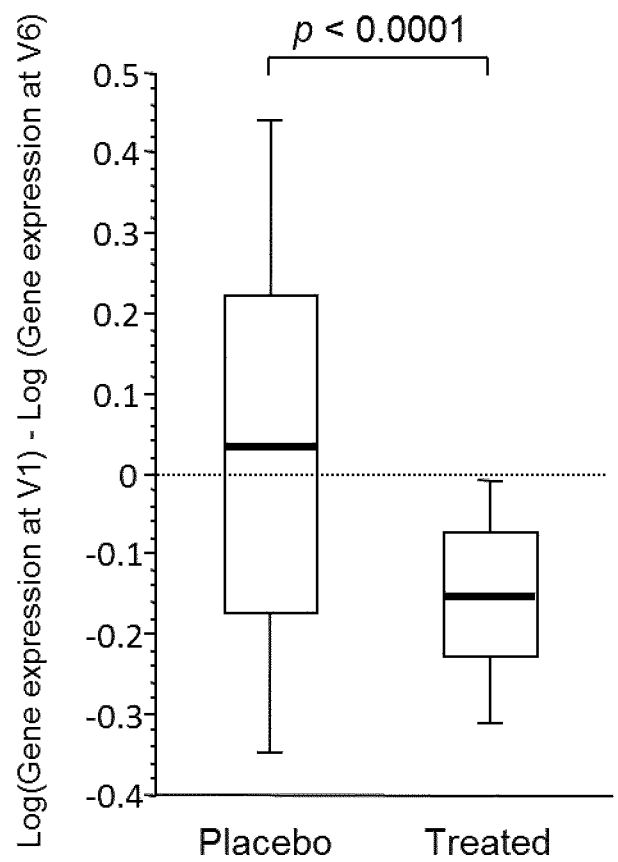
FIG. 2: Differential evolution of IFN-induced genes in treated-versus placebo patients. Out of 11 patients displaying increased levels of IFN-induced gene expression at baseline, 8 were treated with the immunogenic product and 3 received placebo injections. The levels of 250 IFN-induced genes showing the highest levels of over-expression in SLE patients were evaluated using high-density microarrays. The results are depicted as the mean log 2(level of expression at V1)–log 2(level of expression at V6). The p value was calculated using a Student's t-test.
Figure 3:
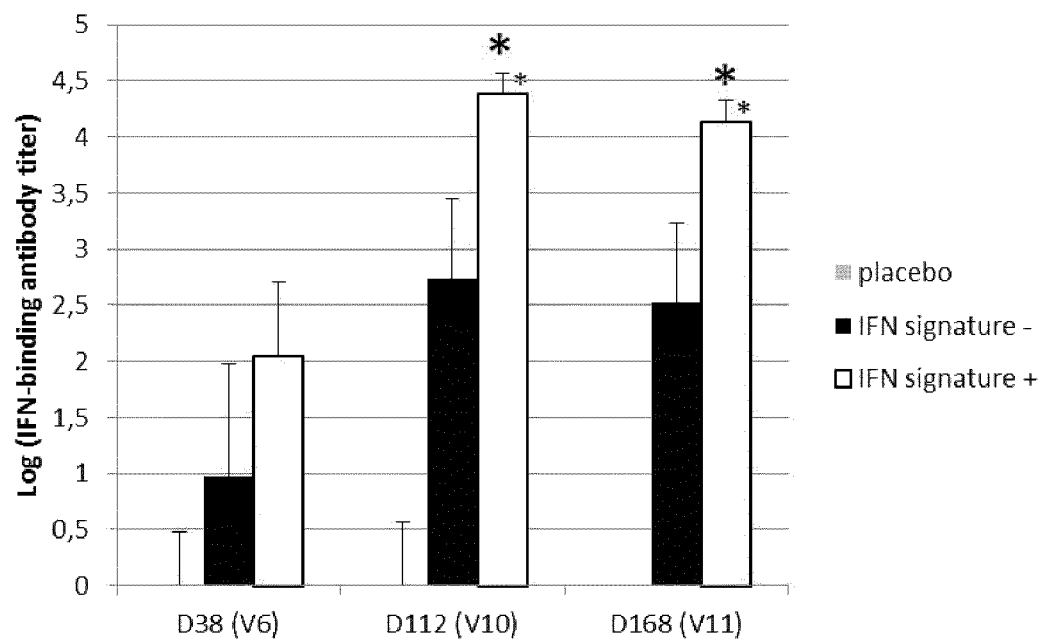
FIG. 3: Titers of IFN-binding antibodies in treated patients with positive or negative IFN-signature at baseline versus placebo receiving patients. Stars indicate p values<0.05.
Figure 4:
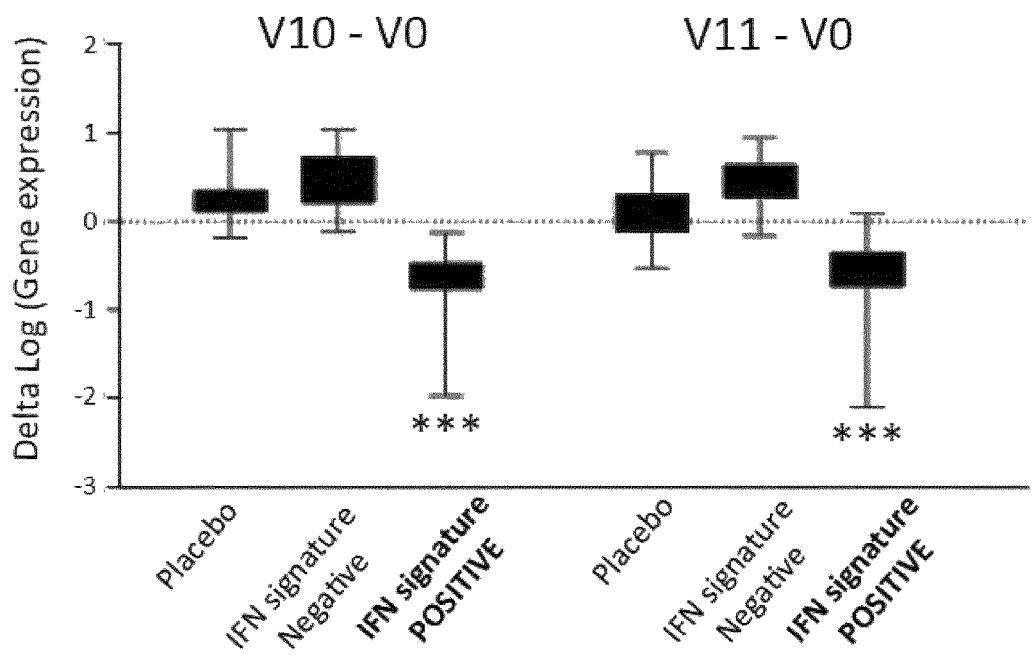
FIG. 4: Differential evolution of IFN-induced genes in treated patients with positive or negative IFN-signature at baseline versus placebo patients, between V10 and V0 or between V11 and V0. The results are depicted as the mean Delta Log (Gene Expression). Stars indicate p values<0.05.
Figure 5:
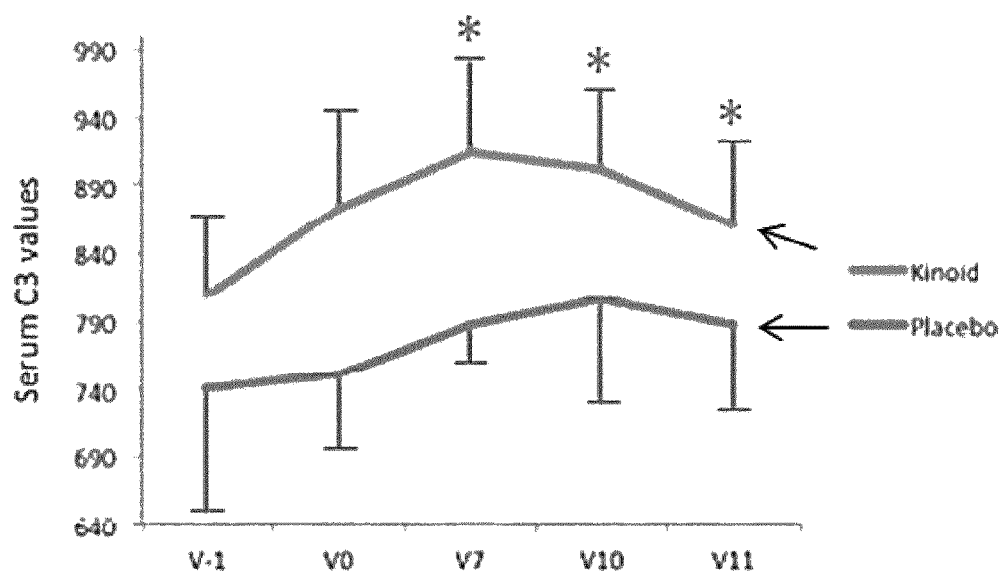
FIG. 5: Evolution of serum C3 values in treated patients with positive IFN-signature at baseline and in placebo receiving patients. Stars indicate p values<0.04.

Example 1: Preparation of the Immunogenic Product

Keyhole Limpet Hemocyanin (KLH) was extracted from the lymph of the marine gastropod mollusk *Megathura crenulata* and then purified under GMP condition.

Results from stability assays performed in storage conditions at a temperature of 2-8° C. showed that the shelf life of the purified KLH is of 36 months at 2-8° C.

Recombinant human IFNα 2b was produced in *E. coli* under GMP conditions.

Batches of the product of the invention at 350 mg IFNα scale were produced using the manufacturing process developed below.

a) Conjugation with Glutaraldehyde

The filtered KLH is added to the IFNα 2b solution (IFNα 2b in 70 mM di-sodium hydrogen phosphate pH 7,8) with a IFNαKLH ratio of 20:1, (corresponding to a molar ratio of 20 monomer of IFNα for 1 subunit of KLH) based on UV concentration.

The conjugation is carried out with glutaraldehyde (added to reach 22.5 mM final concentration in the reaction medium) and borate pH 9 (added to reach 28.5 mM final concentration in the reaction medium), to obtain a pH of 8.5.

This solution at pH 8.5 is then mixed during 45 min at 23±2° C.

b) Quenching with Glycine

The reaction is quenched with Glycine 0.1 M during 30 min.

c) First Tangential Flow Filtration (TFF 1)

The first TFF is performed with a Pall Minim II TFF system and a polyethersulfone membrane of 0.02 m² with a molecular weight cut off of 10 kDa sanitized with 0.5 M NaOH and equilibrated with the working buffer (70 mM di-sodium hydrogen phosphate pH 7,8).

The quenched solution is then clarified by 0.22 μm-filtration. The intermediate is diluted twice in the working buffer and then diafiltered by tangential flow filtration (TFF) and 12 volumes of working buffer. The retentate is harvested and is stored for less than 20 hours.

d) Inactivation with Formaldehyde

Formaldehyde is added to the retentate to reach a final concentration of 66.6 mM using a peristaltic pump. The inactivation reaction is performed during 40 hours in an incubator set to 37±2° C. with a daily mixing of the solution with a magnetic stirrer.

e) Quenching with Glycine

The reaction is then quenched with 0.1 M of Glycine during 30 min.

f) Second Tangential Filtration (TFF 2)

The second TFF is performed with a Pall Minim II TFF system and a polyethersulfone membrane of 0.02 m$^2$ with a molecular weight cut off of 100 kDa sanitized with 0.5 M NaOH and equilibrated with the formulation buffer (70 mM di-sodium hydrogen phosphate pH 7,8).

The quenched solution is clarified by 0.2 m filtration. The intermediate is concentrated to have a starting tangential volume of ≈900 mL and next filtrated by TFF with 12 volumes of formulation buffer (70 mM phosphate buffer) to eliminate the low molecular weight homopolymers of IFNα and the non reactive reagents. The retentate is harvested and then diluted to a theoretical concentration of 300 µg/mL based on concentration determination by Bradford protein assay and then 0.2 µm-filtered to obtain the immunogenic product of the invention.

Example 2: Antigenicity of the Product

A sandwich ELISA anti IFNα/KLH was carried out as following. Briefly, a 96 wells plate was coated with the capture antibody: rabbit polyclonal anti-KLH antibody, and blocked with a blocking buffer (such as casein 2% in PBS for example) during 90 min at 37° C. The plate was incubated during 90 min at 37° C. the plate with a dilution series of the immunogenic product from 250 ng/ml to 8 two fold dilutions or with negative controls such as KLH and IFNα. A detection antibody such as for example a biotinylated anti-IFNα antibody was then added for 90 min. Finally the plate was incubated with streptavidin-HRP during 30 min at 37° C. and the complex developed with an o-phenylenediamine dihydrochloride (OPD) substrate solution during 30 min.

After stopping the enzymatic reaction, the intensity of the resulting color is determined by spectrophotometric methods at 490 nm.

This test confirmed that the product comprises IFNα that is antigenic, i.e. recognized by anti-IFNα antibody and that said IFNα is coupled to KLH.

Example 3: Immunogenicity of the Product (TEST A)

4 µg of total proteins of the product as determined by Bradford protein assay were injected to 7 Balb/c mice of 6-8 weeks at day 0 and day 21.

At day 31, mice were bleeded and the sera were harvested. An anti-IFNα ELISA was carried out on preimmune and harvested sera as following:
- a 96 wells plate was coated with 100 ng of IFNα-2b and incubated overnight at 2° C.-8° C.,
- a blocking buffer was added during 90 min at 37° C.,
- the immunogenic product was added at a dilution of 1/2500 up to at least 8 two fold dilutions and the plate was incubated during 90 min at 37° C.,
- the plate was incubated with an anti-mouse immunoglobulin labeled antibody such as an HRP conjugated antibody during 90 min at 37° C.,
- the ELISA was developed with an o-phenylenediamine dihydrochloride (OPD) substrate solution. After stopping the enzymatic reaction, the intensity of the resulting color was determined by spectrophotometric methods at 490 nm.

This test demonstrated that in the 7 mice, immunization with the immunogenic product led to the presence of anti-IFNα antibodies titers.

Example 4: Residual Activity of the Product (TEST B)

This assay was based on the protective effect of IFNα on the cytopathic effect (CPE) of Vesicular Stomatitis Virus (VSV) on Madin-Darby Bovine Kidney (MDBK) cells.

The immunogenic product and the recombinant IFNα 2b used for preparing the immunogenic product (positive control) were diluted at at least 500 ng/ml and at least 1000 U/ml respectively in Basal medium (RPMI supplemented with 2 mM glutamine, 1 mM sodium pyruvate, 1 mM Hepes). 50 µl of the immunogenic product and the positive control were plated in a 96 wells plate and diluted in a series of two fold dilutions in the Basal medium. 2 10$^4$ MDBK cells were added in each well in 50 µl of Cell medium (RPMI supplemented with 4% FBS, 2 mM glutamine, 1 mM sodium pyruvate and 1 mM Hepes) and the plate was incubated overnight at 37° C., 5% $CO_2$. The virus was then diluted in Basal medium to at least 10 TCID$_{50}$ (Tissue Culture Infection Dose 50: 10 times the dilution to kill 50% of infected cells). The plate was emptied and 100 µl of the diluted virus was added. The plate was then incubated overnight at 37° C., 5% $CO_2$.

At the end of the culture, 20 µl/well of a solution of MTS/PMS (100 µl MTS/5 µl PMS; Promega G5430) were added to the wells and the plate was incubated for another 4 h at 37° C. 5% CO2. The plate was then read at 490 nm on a spectrophotometer.

The percentage of antiviral activity of the immunogenic product was calculated and for the two batches of product tested, the antiviral activity was less than 1% of the antiviral activity of IFNα.

Example 5: Neutralization Capacity of the Product (TEST C)

The neutralizing capacity of the product was assessed by evaluating the cell viability in presence of the vesicular stomatitis virus replicating in MDBK cells.

4 µg of total proteins (as determined by a Bradford protein assay) of the immunogenic product were injected in Balb/c mice of 6-8 weeks at day 0 and day 21. A serum sample was obtained before immunization (pre-immune serum sample) and at day 31 (test serum sample).

25 µl of pre-immune and test serum samples were plated in a 96-well plate at a dilution of 1/200 up to 8 dilutions from 1/200. The positive control (polyclonal anti-IFNα from PBL, Piscataway, N.J., ref. 31100-1) was diluted from 3125 UI/well to 100 UI/well in Basal medium (RPMI supplemented with 2 mM glutamine, 1 mM sodium pyruvate and 1 mM hepes) and 25 µl were also plated in the plate.

25 U/well (final concentration) in 25 µl of basal medium of IFNα was added to each well and the plate is incubated for 60 min at room temperature.

20000 MDBK cells in Assay medium (RPMI supplemented with 4% FBS, 2 mM glutamine, 1 mM sodium pyruvate, 1 mM hepes) were added to each well and the plate was incubated overnight at 37° C., 5% $CO_2$.

The virus was diluted to at least 10 TCID$_{50}$ (10 times the dilution to kill 50% of infected cells) in virus medium (RPMI supplemented with 2 mM glutamine, 1 mM sodium pyruvate, 1 mM hepes). The plate was emptied and 100 μl of virus was added to each well before incubation for 24 h at 37° C., 5% CO$_2$.

At the end of the culture, 20 μl/well of a solution of MTS/PMS (100 μl MTS/5 μl PMS; Promega G5430) were added to the wells and the plate was incubated for another 4 h at 37° C. 5% CO2. The plate was then read at 490 nm on a spectrophotometer.

The NC was calculated for all the 7 test samples: mean NC=253789 IU/ml (SEM=172526), demonstrating that all serum comprised antibodies anti-IFNα capable of neutralizing the antiviral activity of IFNα.

Example 6: Examples of Compositions and Vaccine Comprising the Immunogenic Product One illustrative composition comprising the immunogenic product is described in Table 1.

TABLE 1

| Components | Quantity |
|---|---|
| Product of the invention | 160 μg |
| di-sodium phosphate | 8.95 mg |
| Disodium dihydrogen phosphate | 805 μg |
| Total volume | 0.4 ml |

One illustrative vaccine comprising the immunogenic product is described in Table 2.

TABLE 2

| Emulsion | |
|---|---|
| Components | Quantity |
| Product of the invention | 160 μg |
| di-sodium phosphate | 8.95 mg |
| Disodium dihydrogen phosphate | 805 μg |
| Drakeol 6VR (mineral oil) | 0.30 g |
| Montanide 80 (mannide monooleate) | 0.04 g |
| Total volume | 0.8 ml |

Example 7: Clinical Trial

A clinical trial was carried out using the vaccine composition as described in Table 2.

Study Design:

3 or 4 administrations of the product were performed at day 0, day 7 and day 28 or at day 0, day 7, day 28 and day 84 in adults subjected to SLE.

The following doses of the product were tested: 30 mcg, 60 mcg, 120 mcg and 240 mcg.

Study Population:

28 male or female patients aged between 18 and 50 years, with mild to moderate SLE (SLEDAI 4-10), active disease despite receiving treatment. A normal control interferon gene signature was established in 48 healthy volunteers. PBMC of 18 out of the 48 healthy volunteers were stimulated in vitro with type I interferons in order to identify an interferon signature on the high-density arrays. A SLE signature was established by comparing the signatures between healthy volunteers and SLE patients at baseline.

An interim analysis was performed in the patients enrolled in the first three groups, ie having received the 30, 60 or 120 mcg doses or placebo.

TABLE 3

| Demographics for enrolled patients (interim analysis) | | | | | |
|---|---|---|---|---|---|
| Summary Statistics | Immunogenic product 30 mcg (N = 3) | Immunogenic product 60 mcg (N = 6) | Immunogenic product 120 mcg (N = 6) | Placebo (N = 5) | Total (N = 20) |
| Age (years) | | | | | |
| Mean (SD) | 36.0 (9.85) | 39.3 (3.98) | 34.2 (12.12) | 38.6 (11.52) | 37.1 (9.28) |
| Median | 33.0 | 38.0 | 32.5 | 43.0 | 37.5 |
| Sex, n (%) | | | | | |
| Male | 0 (0.0) | 0 (0.0) | 0 (0.0) | 0 (0.0) | 0 (0.0) |
| Female | 3 (100.0) | 6 (100.0) | 6 (100.0) | 5 (100.0) | 20 (100.0) |
| Race, n (%) | | | | | |
| White-Caucasian | 3 (100.0) | 6 (100.0) | 6 (100.0) | 5 (100.0) | 20 (100.0) |
| SLEDAI-2000 | | | | | |
| Mean | 8.67 (1.15) | 7.50 (2.81) | 6.00 (2.19) | 8.80 (1.09) | |
| Median | 8.00 | 8.50 | 6.00 | 8.00 | |
| Anti-ds DNA ab | | | | | |
| Mean (SD) | 53.93 (58.22) | 61.25 (113.46) | 140.55 (242.63) | 88.70 (113.62) | |
| Median | 33.10 | 15.45 | 23.60 | 40.90 | |
| DURATION OF DISEASE (YEARS) | | | | | |
| Mean (SD) | 10.0 (2.18) | 8.9 (8.82) | 7.3 (5.99) | 5.9 (4.75) | 7.9 (6.11) |
| Median | 11.0 | 6.1 | 6.1 | 3.6 | 6.4 |
| CONCOMMITANT CORTICOSTEROIDS | 100% | 66.7% | 83.3% | 100% | |

TABLE 4

Demographics for enrolled patients (final analysis)

| Measure | | 30 µg N = 3 | 60 µg N = 6 | 120 µg N = 6 | 240 µg N = 6 | Placebo N = 7 |
|---|---|---|---|---|---|---|
| Age (y) | Mean ± SD | 36.0 ± 9.8 | 39.3 ± 4.0 | 34.2 ± 12.1 | 34.8 ± 10.8 | 40.1 ± 10.2 |
| | Median | 33 | 38 | 33 | 36 | 43 |
| | Range | 28-47 | 35-46 | 19-50 | 21-46 | 20-50 |
| Sex | | | | | | |
| Female | n (%) | 3 (100) | 6 (100) | 6 (100) | 6 (100) | 7 (100) |
| Ethnicity | | | | | | |
| White-Caucasian | n (%) | 3 (100) | 6 (100) | 6 (100) | 6 (100) | 6 (85.7) |
| Asian | n (%) | 0 (0.0) | 0 (0.0) | 0 (0.0) | 0 (0.0) | 1 (14.3) |
| Weight (kg) | Mean ± SD | 69.7 ± 11.9 | 67.8 ± 10.0 | 59.2 ± 7.4 | 70.0 ± 15.9 | 57.4 ± 14.8 |
| | Median | 75 | 63 | 59 | 65 | 55 |
| | Range | 56-78 | 58-81 | 51-71 | 54-97 | 46-90 |
| Height (cm) | Mean ± SD | 162.3 ± 6.4 | 165.0 ± 5.1 | 164.0 ± 5.5 | 162.8 ± 8.6 | 162.7 ± 5.8 |
| | Median | 165 | 166 | 165 | 163 | 163 |
| | Range | 155-167 | 159-170 | 156-172 | 152-172 | 153-170 |
| Body mass index (kg/m$^2$) | Mean ± SD | 26.6 ± 6.0 | 25.0 ± 4.3 | 22.1 ± 3.5 | 26.7 ± 7.2 | 21.7 ± 5.2 |
| | Median | 27 | 24 | 21 | 25 | 20 |
| | Range | 21-32 | 21-32 | 18-28 | 20-40 | 17-33 |
| Disease duration (y) | Mean ± SD | 9.9 ± 2.2 | 8.9 ± 8.8 | 7.2 ± 6.0 | 11.8 ± 8.4 | 6.5 ± 4.0 |
| | Range | 7-11 | 1-23 | 0-18 | 2-21 | 1-11 |
| SLEDAI 2000 index | Mean ± SD | 8.7 ± 1.2 | 7.5 ± 2.8 | 6.0 ± 2.2 | 6.0 ± 1.8 | 8.4 ± 1.1 |
| | Range | 8-10 | 4-10 | 4-10 | 4-8 | 7-10 |
| Medications at baseline, n (%) | | | | | | |
| Glucocorticoids | n (%) | 3 (100.0) | 4 (66.7) | 5 (83.3) | 3 (50.0) | 6 (85.7) |
| Aminoquinolines | n (%) | 0 (0.0) | 4 (66.7) | 3 (50.0) | 5 (83.3) | 5 (71.4) |
| Methotrexate | n (%) | 0 (0.0) | 1 (16.7) | 1 (16.7) | 1 (16.7) | 1 (14.3) |
| Azathiopine | n (%) | 0 (0.0) | 1 (16.7) | 1 (16.7) | 1 (16.7) | 0 (0.0) |

Results

Safety and Tolerability of the Vaccine

Two lupus flares have been reported as related SAEs. The first was in the placebo group. The other occurred after the first injection of IFN-K 240 mcg in a patient who had spontaneously stopped her corticosteroid therapy two days after injection. This abrupt stopping of corticosteroids treatment likely participated to the occurrence of the flare. Regular interim safety analyses were performed by an independent safety board. No clinically significant change in laboratory parameters has been detected (hematology, biochemistry, urine).

Immunogenicity of the Vaccine

Anti-IFNα antibody titers were measured by ELISA from serum samples obtained from the patients.

An anti-IFNα ELISA was carried out as described here above.

Results show that anti-IFNα antibody titers were detected in all groups treated with the immunogenic product starting on day 28.

Neutralization Activity of the Vaccine

The neutralization activity was assessed in vitro using the following method:

50 µl of serum samples obtained from the patients sera were plated in a 96-well plate at a dilution of 1/200 up to 8 dilutions from 1/200.

The positive control (polyclonal anti-IFN from PBL Piscataway, N.J., 31100-1) was diluted from 100 ng/well to 3.125 ng/well and 500 were added to the plate. Dilutions were carried out in Basal medium (RPMI supplemented with 2 mM glutamine, 1 mM sodium pyruvate and 1 mM hepes).

10 U/well (final concentration) of IFNα 2b were added to each well and the plate was incubated for 60 min at room temperature.

30000 MDBK cells in Assay medium (RPMI supplemented with 4% FBS, 2 mM glutamine, 1 mM sodium pyruvate, 1 mM hepes) were added to each well and the plate was incubated overnight at 37° C., 5% $CO_2$.

The virus was diluted to at least 10 $TCID_{50}$ (10 times the dilution to kill 50% of infected cells) in virus medium (RPMI supplemented with 2 mM glutamine, 1 mM sodium pyruvate, 1 mM hepes). The plate was emptied and 100 µl of virus was added to each well before incubation for 24 h at 37° C., 5% $CO_2$.

At the end of the culture, 20 µl/well of a solution of MTS/PMS (100 µl MTS/5 µl PMS; Promega G5430) were added to the wells and the plate was incubated for another 4 h at 37° C. 5% CO2. The plate was then read at 490 nm on a spectrophotometer.

The results of interim report showed that none of the sera from patients treated with 30 mcg of the immunogenic product presents anti-IFNα antibodies having a neutralizing capacity at day 168 after immunization, whereas the sera from patients treated with 60 mcg of the immunogenic product present anti-IFNα antibodies having a neutralizing capacity at day 168 (FIG. 1).

Moreover, the results of the final report showed that a neutralizing activity was detected in 50% of subject treated with 60 µg or 120 µg of the immunogenic product, and in 80% of subjects treated with 240 µg of the immunogenic product (Table 5)

TABLE 5

| Dose (mcg) | Number of responder (%) | NC50 median at peak (Dil-1) |
|---|---|---|
| 30 | 0 | 0 |
| 60 | 50 | 390 |

TABLE 5-continued

| Dose (mcg) | Number of responder (%) | NC50 median at peak (Dil-1) |
|---|---|---|
| 120 | 50 | 733 |
| 240 | 80 | 316 |

These results demonstrated that treatment with more than 30 mcg of the immunogenic product is necessary for having an in vivo neutralization of IFNα.

Example 8: Transcriptomic Analysis

PBMC were harvested at several time-points before and after injection of the immunogenic product. For this interim analysis, total RNA was extracted at V1 (day 0) and V6 (day 38 after the first injection) samples, labeled according to standard Affymetrix protocol, and hybridized on GENECHIP® HGU133 Plus 2.0 arrays. Statistical analyses were performed on GENESPRING® after RMA (Robust Microarray Analysis) normalization of the samples.

Unsupervized clustering algorithms were performed on the baseline samples, and grouped the patients in two categories: those with (n=11), and those without (n=7) the presence of an 'Interferon-signature' at baseline, i.e. the spontaneous over-expression of genes induced by type I interferon (the IFN-induced genes were identified experimentally, based on microarray analyses of IFN-stimulated control PBMC). Not surprisingly, dsDNA titers were significantly higher in the patients with the signature (mean+/−SEM: 131.1.+/−50.1 UI/ml), compared to the patients without (mean+/−SEM: 44.7+/−33.3, p=0.006 by Mann-Whitney test). Measurable anti-IFNα antibodies were found in 8 follow-up samples of the 8 patients with an IFN signature at baseline who received the immunogenic product, while this was only the case in 2 out of 6 patients without IFN signature treated with the immunogenic product, and none out of the 4 placebo-treated individuals (p=0.002 by Chi-squared test). Out of the 11 patients with a baseline IFN-signature, 2 received the 30 mcg dose, 1 received the 60 mcg dose, 5 received the 120 mcg dose and 3 were treated with a placebo injection. The changes observed in the expression of the IFN-induced genes between V1 and V6 were significantly different in the patients treated with the immunogenic product, as compared to the patients treated with the placebo (FIG. 2).

This result suggests that the immunogenic product has an effect on the expression of IFN-induced genes in vivo.

Example 9: IFN Signature and Response to Immunogenic Product-Treatment

The "Interferon-signature" at baseline was measured in the 28 patients with mild to moderate SLE of Example 7. The Interferon-signature (IFN-signature) corresponds to a score calculated using 21 IFN-induced genes, and was described in Yao et al, Arthritis & Rheumatism, 2009, 60 (6): 1785-1796. Measurement of the Interferon-signature was done as described in Example 8.

On the 28 SLE patients of Example 7, 19 showed a positive Interferon-signature and 9 a negative Interferon signature at baseline.

Interferon Signature and SLE Disease Activity dsDNA antibody titers and serum levels of C3 were measured as indices of disease activity in both groups of patients.

dsDNA Antibody titers were determined using DPC Anti-DNA kit (PIKADD-4) from Diagnostic Products Corporation.

C3 serum levels were determined using Complement C3 kit (Kit #446450) from Beckman Coulter.

TABLE 6

| Indices of SLE disease activity | | | |
|---|---|---|---|
| | IFN signature positive SLE | IFN signature negative SLE | p value |
| dsDNA Ab | 147 ± 57 | 44 ± 93 | <0.05 |
| C3 | 834 ± 55 | 1199 ± 114 | <0.005 |

As shown in the Table 6 above, SLE patients with positive Interferon-signature at baseline have biological indices of higher disease activity.

Interferon-Signature and Response to Treatment with the Immunogenic Product of the Invention The effects of the treatment with the immunogenic product of the invention as described in Example 7 were compared in SLE patients with positive and negative IFN-signature at baseline.

Anti-IFN-Alpha Response

IFN-binding antibody titers were measured as described in Example 7 at V6 (day 38), V10 (day 112) and V11 (day 168 after immunization).

The results showed that SLE patients with positive Interferon-signature produce ten folds more IFN-binding antibodies in response to the immunogenic product of the invention than SLE patients with negative Interferon-signature at baseline (FIG. 3).

IFN-Induced Genes

The evolution of the expression of IFN-induced genes between V0 and V10 or V11 was measured in treated patients with positive or negative IFN signature at baseline and in patients treated with placebo.

The results showed that compared to placebo and IFN-signature negative patients, the effects of therapy with the immunogenic product of the invention on IFN-induced genes were strongly and significantly different at V10 and V11 in IFN-signature positive SLE patients (FIG. 4).

Complement C3

Serum C3 values were measured in treated patients and in placebo receiving patients at V-1 (30 days before immunization), V0 (day of immunization), V7 (day 56), V10 (day 112) and V11 (day 138 after immunization) as hereinabove described.

Results showed that there is a significant increase in C3 levels in treated-versus placebo patients. Moreover, there is a significant increase in C3 levels in IFN-signature positive SLE patients treated with the immunogenic product of the invention (FIG. 5).

Example 10: Determination of the Ratio IFNα/KLH in the Product of the Invention

In order to assess the amount of IFNα and KLH in the product of the invention, a method of quantification based on UV and fluorescence detection was developed. The products of the invention were manufactured with two fluorescent labels, each specific of IFNα or KLH. After analysis by Size Exclusion Chromatography (SEC), quantification of IFNα and KLH was determined by integration of the UV signal at 220 nm and fluorescent signal (FLD) specific for IFNα label or KLH label. This method allowed calculating the ratio in weight of IFNα/KLH.

a) Raw Materials Labeling:

Fluorescent tags were coupled on sulfhydryl groups in order to preserve amino groups used during the product manufacturing.

Labeling was conducted in 70 mM pH7 sodium phosphate buffer at room temperature during 3 h. KLH were labeled with 200 molar equivalent of Atto565-maleimide (18507, Sigma) and IFNα with 100 molar equivalent of fluorescein maleimide (46130, Pierce). The labeled proteins (KLH-atto565 and IFN-Fluorescein) were then filtrated on Zeba column (cut off 7 kDa, Thermo Scientific, 89893) conditioned with 70 mM pH 7.8 phosphate buffer in order to eliminate unreacted tags.

b) Product Manufacturing:

The labeled raw materials were then used to manufacture labeled products with the same process as in Example 1 with dialysis filtration instead of tangential flow filtration.

c) KLH and IFNα Homopolymers Standards Manufacturing

For the quantitative analytical method, homopolymers standards were manufactured.

Labeled IFNα homopolymers standard was manufactured with the same process as in Example 1 but with 70 mM phosphate buffer pH 7.8 instead of KLH and dialysis filtration instead of tangential flow filtration.

Labeled KLH homopolymers standard was manufactured with the same process as in Example 1 but with 70 mM phosphate buffer pH 7.8 instead of IFNα and dialysis filtration instead of tangential flow filtration.

d) Method Analysis by Size Exclusion Chromatography

Batches were then analyzed by SEC with UV and specific fluorescent detection. 60 µL of sample was injected on columns SEC5 (1000 A°) SEC3 (300 A°) connected in series (Agilent, 5190-2536, 5190-2511), elution was performed with PBS during 35 min with UV detection at 220 nm and specific fluorescent detection (for IFNα-Fluorescein or KLH-Atto565), as described Table 7.

TABLE 7

Excitation and emission wavelength used for IFNα-Fluorescein or KLH-Atto-565

| Fluorescent specific | wavelength nm | |
|---|---|---|
| detection | Excitation | Emission |
| IFN$_\alpha$-Fluorescein | 490 | 520 |
| KLH-Atto565 | 570 | 600 |

UV and fluorescent (FLD) signals were calculated by integrating the area under the chromatogram peaks between 0 and 20 min.

To validate this method, preliminary experiments were conducted to demonstrate:

Fluorescent signal specificity (no signal overlapping was observed between the two labeled proteins), For each manufactured batch (product of the invention, labeled homopolymers of KLH and IFNα), similar UV profiles by SE-HPLC were obtained, No quenching of the fluorescent signal due to the manufacturing was observed, FLD signals were linear and proportional to UV signals.

Labeled IFNα UV contribution in the manufactured labeled kinoid was measured according to the curve Area by $FLD_{IFN\alpha-Fluorescein}$=f(Area by UV) of labeled IFNα homopolymers standard.

Labeled KLH UV contribution in the manufactured labeled kinoid was measured according to the curve Area by $FLD_{KLH-Atto565}$=f(Area by UV) of labeled KLH homopolymers standard.

As UV area was checked to be a linear function of protein concentration, this method allowed assessing the percentage in weight of labeled IFNα in the total manufactured labeled kinoid.

e) Batches Analysis 3 batches of labeled kinoids were manufactured and analyzed by this method.

Based on the proportionality of UV signal and concentration, and of FLD and UV signal, the ratio between the amount of IFNα and KLH (mIFNα/mKLH) was calculated for the three batches (Table 8).

TABLE 8 weight ratio of IFNα/KLH in the three labeled kinoid manufactured

| | Ratio $m_{IFN}/m_{KLH}$ | Mean | RSD % |
|---|---|---|---|
| Batch 1 | 0.29 | 0.28 | 12 |
| Batch 2 | 0.31 | | |
| Batch 3 | 0.25 | | |

A mean ratio mIFNα/mKLH of 0.28 was found with a relative standard deviation <15%.

Example 11: Anti-mIFNα Antibodies Titers Produced and Neutralizing Capacities when Immunogenic Product of the Invention is Injected as an Emulsion with SWE or SWE-a Manufacturing muIFN-K:

Briefly, murine IFNαA (PBL Biomedical Laboratories) and native KLH (Sigma) were mixed at a 50:1 ratio and treated with 22.5 mM glutaraldehyde for 45 minutes. After dialysis against phosphate-buffered saline (PBS) to eliminate excess glutaraldehyde, the solution was incubated with 66 mM formaldehyde for 48 hours at 37° C. After quenching with glycine (0.1 M final) and subsequent dialysed against PBS using a 10-kDa cutoff membrane, the preparation was filter-sterilized using a 0.22-µm membrane and stored at 4° C.

Immunization Protocol:

Mice were immunized i.m. twice at day 0 and day 21 with mIFN-K (10 µg per injection) as an emulsion 1 to 1 with SE or SE-a adjuvant (100 µl final volume).

Determination of Anti-muIFNα and Anti-KLH Antibody Titers by ELISA

Sera were analyzed for antibodies against muIFNα or KLH by ELISA. Briefly, 96-well Maxisorp plates (Nunc) were coated with 100 ng/well of muIFNαA (PBL Biomedical Laboratories) to detect anti-muIFNα antibodies or native KLH (Sigma) to detect anti-KLH antibodies.

Two-fold serial serum samples dilution (from 1:100 to 1:51, 200) were added to the wells. Blank wells received 100 µL of dilution buffer. After 1.5 hours at 37° C., antibodies were detected with 100 µL of horseradish peroxidase-conjugated anti-mouse immunoglobulin G (IgG) and O-phenylenediamine, a colorimetric substrate for horseradish peroxidase. A pool of sera from muIFN-K immunized Balb/c mice was used as a positive control. The optical density (OD) was recorded at a wavelength of 490 nm. ELISA assays were performed in duplicate. In each plate, two wells were reserved for blanks; their mean value was subtracted from all wells.

Antibody titers were calculated by interpolating the maximum OD (ODmax)/2 on the x-axis. The equation used was y=ax+b for a straight line passing through two points surrounding the ODmax/2.

Determination of Neutralizing Capacity of Anti-muIFNα Antibodies Induced after IFN-K Immunizations Neutralizing capacity was determined using the classical antiviral cytopathic assay (EMCV/L929). In this assay, the antiviral activity titer of muIFNα is determined regarding its capacity to inhibit the lethal effect of encephalomyocarditis virus (EMCV) on murine L-929 cells (ATCC).

Briefly, 25 µL of diluted serum samples (or control antibody) were added to 96-well culture plates (Nunc) in two-fold serial dilutions (from 1:200 to 1:6400). A commercial rabbit polyclonal antibody anti-muIFNα (from PBL, ref: 32100-1) was used as a positive control. After incubation with 25 IU/well of muIFNα for 1 hour at room temperature, 20×10³ L-929 cells were seeded per well and incubated at 37° C. After overnight growth, plates were washed with PBS and 100 µL/well of EMCV solution (100 times the dose needed to kill 50% of the cells) was added to each well. Plates were incubated during 48 hours at 37° C. Finally, 20 µL per well of MTS/PMS (3-(4,5-dimethylthiazol-2-yl)-5-(3-carboxymethoxyphenyl)-2-(4-sulfophenyl)-2H-tetrazolium, inner sal/phenazine methosulfate) solution (Promega) was added and the plates were incubated for 4 h at 37° C., 5% CO2 in a humidified incubator (protected from light). Next, the OD at 490 nm was measured for each well. The OD of the blank (wells with 100 µL of culture medium alone) was subtracted from the sample OD.

The neutralizing capacity of each sample was calculated as following:

Neutralizing capacity (%)=100×[(OD test−OD virus)/(OD cells)], where

ODtest is the OD for the tested sample (cells+IFNα+serum+virus)

ODvirus is the OD for the virus control (cells+virus)

ODcells is the OD for 20,000 cells/well (cells+IFNα+virus).

Neutralizing capacities were plotted as a function of serum dilution. The titer (number of serum dilution) neutralizing 50% of IFNα activity values were determined by interpolation on the linear part of the curve.

Results showed that anti-muIFNα titers and anti-KLH titers were present in mice sera collected at day 31 after first injection of muIFN-K emulsified in SWE or SWE-a; and that the anti-muIFNα antibodies had neutralizing capacities (NC50>200).

The invention claimed is:

1. A method for treating systemic lupus erythematosus (SLE), Sjögren syndrome, type I diabetes, dermatomyositis and/or polymyositis in a subject in need thereof, by raising antibody levels against IFNα, the method comprising administering to the subject a therapeutically effective amount of an immunogenic product comprising IFNα coupled to keyhole limpet hemocyanin (KLH),
    wherein said therapeutically effective amount is in the range of from 60 mcg to 240 mcg of immunogenic product per administration, and wherein the weight ratio of IFNα/KLH is in the range of 0.06 to 0.6, and
    wherein said treating means at least one selected from the group consisting of alleviating symptoms, suppressing, diminishing or inhibiting any direct or indirect pathological consequences of the IFNα related condition, lowering the rate of progression of the IFNα related condition, ameliorating or palliating the state of the IFNα related condition, causing remission, maintaining remission state and improving prognosis.

2. The method according to claim 1, wherein the immunogenic product is administrated to the subject at least twice in a month.

3. The method according to claim 1, wherein the immunogenic product is administrated to the subject at least twice in a month, and then thereafter administrated to the subject at least once every three months.

4. The method according to claim 2, wherein the immunogenic product is further administrated to the subject when, in a serum sample obtained from the subject, the amount of anti-IFNα antibodies is undetectable when quantified by ELISA or by bioassay to detect neutralizing anti-IFNα antibodies.

5. The method according to claim 1, wherein the immunogenic product shows less than 5% of antiviral activity in the conditions of TEST B, wherein said TEST B is based on the protective effect of IFN on the cytopathic effect of vesicular stomatitis virus on Madin-Darby Bovine Kidney cells.

6. The method according to claim 1, wherein the immunogenic product is capable of neutralizing the antiviral activity of IFNα in the conditions of TEST C, wherein said TEST C consists in evaluating the neutralizing capacity of the serum obtained from mice immunized with the immunogenic product by evaluating the cell viability in presence of the vesicular stomatitis virus replicating in Madin-Darby Bovine Kidney cells.

7. The method according to claim 1, wherein the immunogenic product comprises at least one subtype of IFNα.

8. The method according to claim 1, wherein the immunogenic product comprises the subtype IFNα 2b or 2a of IFNα.

9. The method according to claim 1, wherein the immunogenic product is a vaccine, preferably in the form of an emulsion.

10. The method according to claim 1, wherein said IFNα related condition is systemic lupus erythematosus (SLE).

11. The method according to claim 1, wherein said IFNα related condition is Sjögren syndrome.

12. The method according to claim 1, wherein said IFNα related condition is dermatomyositis and polymyositis.

13. The method according to claim 1, wherein said IFNα related condition is type I diabetes.

* * * * *